United States Patent
Blanchard

(10) Patent No.: US 8,337,484 B2
(45) Date of Patent: Dec. 25, 2012

(54) PROXIMALLY TRIMMABLE CATHETER INCLUDING PRE-ATTACHED BIFURCATION AND RELATED METHODS

(75) Inventor: Daniel B. Blanchard, Bountiful, UT (US)

(73) Assignee: C. R. Band, Inc., Murray Hill, NJ (US)

( * ) Notice: Subject to any disclaimer, the term of this patent is extended or adjusted under 35 U.S.C. 154(b) by 134 days.

(21) Appl. No.: 12/823,663

(22) Filed: Jun. 25, 2010

(65) Prior Publication Data
US 2010/0331823 A1 Dec. 30, 2010

Related U.S. Application Data

(60) Provisional application No. 61/220,943, filed on Jun. 26, 2009.

(51) Int. Cl.
*A61M 25/18* (2006.01)
(52) U.S. Cl. ..................................... 604/533
(58) Field of Classification Search .......... 604/523–532, 604/533, 164.03
See application file for complete search history.

(56) References Cited

U.S. PATENT DOCUMENTS

| | | | |
|---|---|---|---|
| 2,471,623 A | 5/1949 | Hubbell |
| 2,709,542 A | 5/1955 | Eller |
| 3,176,690 A | 4/1965 | H'Doubler |
| D217,795 S | 6/1970 | Spaven |
| 3,527,226 A | 9/1970 | Hakim |
| 3,565,078 A | 2/1971 | Vailliancourt et al. |
| 3,572,340 A | 3/1971 | Lloyd et al. |
| 3,650,507 A | 3/1972 | Nyberg et al. |
| 3,672,372 A | 6/1972 | Heimlich |
| 3,805,794 A | 4/1974 | Schlesinger |
| 3,921,631 A | 11/1975 | Thompson |
| 4,000,739 A | 1/1977 | Stevens |
| 4,029,095 A | 6/1977 | Pena et al. |
| 4,068,659 A | 1/1978 | Moorehead |
| 4,112,949 A | 9/1978 | Rosenthal et al. |
| 4,123,091 A | 10/1978 | Cosentino et al. |
| 4,134,402 A | 1/1979 | Mahurkar |

(Continued)

FOREIGN PATENT DOCUMENTS

EP 0183396 A1 6/1986

(Continued)

OTHER PUBLICATIONS

PCT/US2010/040084 filed Jun. 25, 2010 Search Report dated Sep. 27, 2010.

(Continued)

*Primary Examiner* — Kevin C Sirmons
*Assistant Examiner* — Imani Hayman
(74) *Attorney, Agent, or Firm* — Rutan & Tucker, LLP

(57) ABSTRACT

A proximally trimmable catheter is disclosed. In one embodiment, the catheter includes a multi-lumen catheter tube, one or more extension tubes, and a hub for fluidly connecting the two. In a first unlocked state, the hub is axially slidable along the catheter tube. The hub includes tube pins that are in fluid communication with the extension tubes. A cutting member is positioned to longitudinally cut the catheter tube during axial sliding of the hub along the catheter tube such that distal portions of the tube pins remain disposed within the lumens of the catheter tube. When positioned as desired, the hub is locked into a second locked state and is no longer axially slidable along the catheter tube. The tube pins are fluidly sealed within the lumens of the catheter tube as to establish fluid communication between the extension tubes and the lumens via the tube pins.

20 Claims, 23 Drawing Sheets

U.S. PATENT DOCUMENTS

| | | |
|---|---|---|
| 4,198,973 A | 4/1980 | Millet |
| 4,233,974 A | 11/1980 | Desecki et al. |
| 4,235,232 A | 11/1980 | Spaven et al. |
| 4,256,106 A | 3/1981 | Shoor |
| 4,256,116 A | 3/1981 | Meretsky et al. |
| 4,267,835 A | 5/1981 | Barger et al. |
| 4,296,747 A | 10/1981 | Ogle |
| 4,306,562 A | 12/1981 | Osborne |
| 4,340,052 A | 7/1982 | Dennehey et al. |
| 4,387,879 A | 6/1983 | Tauschinski et al. |
| 4,391,029 A | 7/1983 | Czuba et al. |
| 4,411,654 A | 10/1983 | Boarini et al. |
| 4,412,832 A | 11/1983 | Kling et al. |
| 4,424,833 A | 1/1984 | Spector et al. |
| D272,651 S | 2/1984 | Mahurkar |
| 4,430,081 A | 2/1984 | Timmermans |
| 4,431,426 A | 2/1984 | Groshong et al. |
| 4,432,759 A | 2/1984 | Gross et al. |
| 4,436,519 A | 3/1984 | O'Neill |
| 4,439,179 A | 3/1984 | Lueders et al. |
| 4,445,893 A | 5/1984 | Bodicky |
| 4,449,973 A | 5/1984 | Luther |
| 4,468,224 A | 8/1984 | Enzmann et al. |
| 4,473,067 A | 9/1984 | Schiff |
| 4,490,003 A | 12/1984 | Robinson |
| RE31,855 E | 3/1985 | Osborne |
| 4,502,502 A | 3/1985 | Krug |
| 4,512,766 A | 4/1985 | Vailancourt |
| 4,535,818 A | 8/1985 | Duncan et al. |
| 4,539,003 A | 9/1985 | Tucker |
| 4,543,087 A | 9/1985 | Sommercorn et al. |
| 4,553,959 A | 11/1985 | Hickey et al. |
| 4,557,261 A | 12/1985 | Rugheimer et al. |
| 4,568,329 A | 2/1986 | Mahurkar |
| 4,571,241 A | 2/1986 | Christopher |
| 4,573,974 A | 3/1986 | Ruschke |
| 4,581,012 A | 4/1986 | Brown et al. |
| 4,581,025 A | 4/1986 | Timmermans |
| 4,583,968 A | 4/1986 | Mahurkar |
| 4,591,355 A | 5/1986 | Hilse |
| 4,592,749 A | 6/1986 | Ebling et al. |
| 4,596,559 A | 6/1986 | Fleischhacker |
| 4,596,571 A | 6/1986 | Bellotti et al. |
| 4,610,665 A | 9/1986 | Matsumoto et al. |
| 4,619,643 A | 10/1986 | Bai |
| 4,623,327 A | 11/1986 | Mahurkar |
| 4,626,245 A | 12/1986 | Weinstein |
| 4,643,711 A | 2/1987 | Bates |
| 4,650,472 A | 3/1987 | Bates |
| 4,673,393 A | 6/1987 | Suzuki et al. |
| 4,675,004 A | 6/1987 | Hadford et al. |
| 4,675,020 A | 6/1987 | McPhee |
| 4,681,122 A | 7/1987 | Winters et al. |
| 4,682,978 A | 7/1987 | Martin et al. |
| 4,692,141 A | 9/1987 | Mahurkar |
| 4,701,159 A | 10/1987 | Brown et al. |
| 4,722,725 A | 2/1988 | Sawyer et al. |
| 4,723,550 A | 2/1988 | Bales et al. |
| 4,723,948 A | 2/1988 | Clark et al. |
| 4,726,374 A | 2/1988 | Bales et al. |
| 4,738,658 A | 4/1988 | Magro et al. |
| 4,743,265 A | 5/1988 | Whitehouse et al. |
| 4,747,833 A | 5/1988 | Kousai et al. |
| 4,753,765 A | 6/1988 | Pande |
| 4,770,652 A | 9/1988 | Mahurkar |
| 4,772,266 A | 9/1988 | Groshong |
| 4,772,268 A | 9/1988 | Bates |
| 4,776,841 A | 10/1988 | Catalano |
| 4,784,644 A | 11/1988 | Sawyer et al. |
| 4,795,426 A | 1/1989 | Jones |
| 4,798,594 A | 1/1989 | Hillstead |
| 4,808,155 A | 2/1989 | Mahurkar |
| 4,842,582 A | 6/1989 | Mahurkar |
| 4,842,592 A | 6/1989 | Caggiani et al. |
| 4,850,955 A | 7/1989 | Newkirk |
| 4,865,593 A | 9/1989 | Ogawa et al. |
| 4,874,377 A | 10/1989 | Newgard et al. |
| 4,895,561 A | 1/1990 | Mahurkar |
| 4,895,570 A | 1/1990 | Larkin |
| 4,898,669 A | 2/1990 | Tesio |
| 4,909,798 A | 3/1990 | Fleischhacker et al. |
| RE33,219 E | 5/1990 | Daniell et al. |
| 4,921,479 A | 5/1990 | Grayzel |
| 4,929,235 A | 5/1990 | Merry et al. |
| 4,929,236 A | 5/1990 | Sampson |
| 4,932,633 A | 6/1990 | Johnson et al. |
| 4,932,938 A | 6/1990 | Goldberg et al. |
| 4,935,010 A | 6/1990 | Cox et al. |
| 4,936,826 A | 6/1990 | Amarasinghe |
| 4,946,133 A | 8/1990 | Johnson et al. |
| 4,946,449 A | 8/1990 | Davis, Jr. |
| 4,952,359 A | 8/1990 | Wells |
| 4,960,412 A | 10/1990 | Fink |
| 4,966,588 A | 10/1990 | Rayman et al. |
| 4,983,168 A | 1/1991 | Moorehead |
| 4,997,424 A | 3/1991 | Little |
| 5,007,901 A | 4/1991 | Shields |
| 5,035,686 A | 7/1991 | Crittenden et al. |
| 5,041,095 A | 8/1991 | Littrell |
| 5,053,003 A | 10/1991 | Dadson et al. |
| 5,053,004 A | 10/1991 | Markel et al. |
| 5,053,013 A | 10/1991 | Ensminger et al. |
| 5,053,014 A | 10/1991 | Van Heugten |
| 5,053,023 A | 10/1991 | Martin |
| 5,057,073 A | 10/1991 | Martin |
| 5,059,170 A | 10/1991 | Cameron |
| 5,064,414 A | 11/1991 | Revane |
| 5,066,285 A | 11/1991 | Hillstead |
| 5,071,411 A | 12/1991 | Hillstead |
| 5,078,688 A | 1/1992 | Lobodzinski et al. |
| 5,085,645 A | 2/1992 | Purdy et al. |
| 5,092,857 A | 3/1992 | Fleischhacker |
| 5,098,392 A | 3/1992 | Fleischhacker et al. |
| 5,098,393 A | 3/1992 | Amplatz et al. |
| 5,106,368 A | 4/1992 | Uldall et al. |
| 5,108,380 A | 4/1992 | Herlitze et al. |
| 5,112,301 A | 5/1992 | Fenton, Jr. et al. |
| 5,112,323 A | 5/1992 | Winkler et al. |
| 5,114,408 A | 5/1992 | Fleischhaker et al. |
| 5,117,836 A | 6/1992 | Millar |
| 5,125,904 A | 6/1992 | Lee |
| 5,135,599 A | 8/1992 | Martin et al. |
| 5,137,524 A | 8/1992 | Lynn et al. |
| 5,141,497 A | 8/1992 | Erskine |
| 5,149,327 A | 9/1992 | Oshiyama et al. |
| 5,154,701 A | 10/1992 | Cheer et al. |
| 5,156,592 A | 10/1992 | Martin et al. |
| 5,156,596 A | 10/1992 | Balbierz et al. |
| 5,158,545 A | 10/1992 | Trudell et al. |
| 5,158,553 A | 10/1992 | Berry et al. |
| 5,160,323 A | 11/1992 | Andrew et al. |
| 5,163,903 A | 11/1992 | Crittenden et al. |
| 5,167,634 A | 12/1992 | Corrigan, Jr. et al. |
| 5,167,637 E | 12/1992 | Okada et al. |
| 5,169,393 A | 12/1992 | Moorehead et al. |
| 5,171,222 A | 12/1992 | Euteneuer et al. |
| 5,180,372 A | 1/1993 | Vegoe et al. |
| 5,186,431 A | 2/1993 | Tamari |
| 5,188,593 A | 2/1993 | Martin |
| 5,190,520 A | 3/1993 | Fenton, Jr. et al. |
| 5,190,528 A | 3/1993 | Fonger et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,976 A | 3/1993 | Herweck et al. |
| 5,201,722 A | 4/1993 | Moorehead et al. |
| 5,205,834 A | 4/1993 | Moorehead et al. |
| 5,207,650 A | 5/1993 | Martin |
| 5,209,723 A | 5/1993 | Twardowski et al. |
| 5,211,633 A | 5/1993 | Stouder, Jr. |
| 5,215,538 A | 6/1993 | Larkin |
| 5,221,255 A | 6/1993 | Mahurkar et al. |
| 5,221,256 A | 6/1993 | Mahurkar |
| 5,221,263 A | 6/1993 | Sinko et al. |
| 5,234,410 A | 8/1993 | Graham et al. |
| 5,242,413 A | 9/1993 | Heiliger |

| | | | | | |
|---|---|---|---|---|---|
| 5,242,430 A | 9/1993 | Arenas et al. | 5,520,665 A | 5/1996 | Fleetwood et al. |
| 5,250,033 A | 10/1993 | Evans et al. | 5,522,806 A | 6/1996 | Schonbachler et al. |
| 5,251,873 A | 10/1993 | Atkinson et al. | 5,536,255 A | 7/1996 | Moss |
| 5,255,691 A | 10/1993 | Otten | 5,538,505 A | 7/1996 | Weinstein et al. |
| 5,273,540 A | 12/1993 | Luther et al. | 5,542,931 A | 8/1996 | Gravener et al. |
| 5,273,546 A | 12/1993 | McLaughlin et al. | 5,556,387 A | 9/1996 | Mollenauer et al. |
| 5,275,583 A | 1/1994 | Crainich | 5,569,182 A | 10/1996 | Twardowski et al. |
| 5,279,597 A | 1/1994 | Dassa et al. | 5,599,305 A | 2/1997 | Hermann et al. |
| 5,290,294 A | 3/1994 | Cox et al. | 5,599,311 A | 2/1997 | Raulerson |
| 5,304,142 A | 4/1994 | Liebl et al. | 5,613,953 A | 3/1997 | Pohndorf |
| 5,304,156 A | 4/1994 | Sylvanowicz et al. | 5,613,956 A | 3/1997 | Patterson et al. |
| 5,312,337 A | 5/1994 | Flaherty et al. | 5,624,413 A | 4/1997 | Markel et al. |
| 5,312,355 A | 5/1994 | Lee | 5,632,729 A | 5/1997 | Cai et al. |
| 5,312,357 A | 5/1994 | Buijs et al. | 5,636,875 A | 6/1997 | Wasser et al. |
| 5,320,602 A | 6/1994 | Karpiel | 5,637,102 A | 6/1997 | Tolkoff et al. |
| 5,324,271 A | 6/1994 | Abiuso et al. | 5,647,857 A | 7/1997 | Anderson et al. |
| 5,324,274 A | 6/1994 | Martin | 5,651,776 A | 7/1997 | Appling et al. |
| 5,330,437 A | 7/1994 | Durman | 5,653,698 A | 8/1997 | Niedospial et al. |
| 5,334,157 A | 8/1994 | Klein et al. | 5,672,158 A | 9/1997 | Okada et al. |
| 5,334,187 A | 8/1994 | Fischell et al. | 5,685,856 A | 11/1997 | Lehrer |
| 5,336,192 A | 8/1994 | Palestrant | 5,685,867 A | 11/1997 | Twardowski et al. |
| 5,338,313 A | 8/1994 | Mollenauer et al. | 5,702,370 A | 12/1997 | Sylvanowicz et al. |
| 5,342,386 A | 8/1994 | Trotta | 5,702,374 A | 12/1997 | Johnson |
| 5,348,537 A | 9/1994 | Wiesner et al. | 5,704,915 A | 1/1998 | Melsky et al. |
| 5,350,358 A | 9/1994 | Martin | 5,713,867 A | 2/1998 | Morris |
| 5,350,362 A | 9/1994 | Stouder, Jr. | 5,718,678 A | 2/1998 | Fleming, III |
| 5,350,363 A | 9/1994 | Goode et al. | 5,718,692 A | 2/1998 | Schon et al. |
| 5,360,397 A | 11/1994 | Pinchuk | 5,725,506 A | 3/1998 | Freeman et al. |
| 5,360,403 A | 11/1994 | Mische | 5,735,819 A | 4/1998 | Elliott |
| 5,364,393 A | 11/1994 | Auth et al. | 5,741,233 A | 4/1998 | Riddle et al. |
| 5,368,574 A | 11/1994 | Antonacci et al. | 5,752,937 A | 5/1998 | Otten et al. |
| 5,374,245 A | 12/1994 | Mahurkar | 5,755,693 A | 5/1998 | Walker et al. |
| 5,378,230 A | 1/1995 | Mahurkar | 5,755,702 A | 5/1998 | Hillstead et al. |
| 5,380,276 A | 1/1995 | Miller et al. | 5,766,203 A | 6/1998 | Imran et al. |
| 5,382,241 A | 1/1995 | Choudhury et al. | 5,772,628 A | 6/1998 | Bacich et al. |
| 5,389,090 A | 2/1995 | Fischell et al. | 5,772,643 A | 6/1998 | Howell et al. |
| 5,391,152 A | 2/1995 | Patterson | 5,772,678 A | 6/1998 | Thomason et al. |
| 5,395,352 A | 3/1995 | Penny | 5,776,111 A | 7/1998 | Tesio |
| 5,397,311 A | 3/1995 | Walker et al. | 5,782,505 A | 7/1998 | Brooks et al. |
| 5,399,172 A | 3/1995 | Martin et al. | 5,782,807 A | 7/1998 | Falvai et al. |
| 5,401,245 A | 3/1995 | Haining | 5,782,817 A | 7/1998 | Franzel et al. |
| 5,405,320 A | 4/1995 | Twardowski et al. | 5,785,694 A | 7/1998 | Cohen et al. |
| 5,405,323 A | 4/1995 | Rogers et al. | 5,797,869 A | 8/1998 | Martin et al. |
| 5,405,341 A | 4/1995 | Martin | 5,800,414 A | 9/1998 | Cazal et al. |
| 5,407,434 A | 4/1995 | Gross | 5,807,311 A | 9/1998 | Palestrant |
| 5,409,463 A | 4/1995 | Thomas et al. | 5,810,789 A | 9/1998 | Powers et al. |
| 5,409,464 A | 4/1995 | Villalobos | 5,830,184 A | 11/1998 | Basta |
| 5,409,469 A | 4/1995 | Schaerf | 5,843,031 A | 12/1998 | Hermann et al. |
| 5,409,644 A | 4/1995 | Martin et al. | 5,843,046 A | 12/1998 | Motisi et al. |
| 5,413,561 A | 5/1995 | Fischell et al. | 5,853,393 A | 12/1998 | Bogert |
| 5,415,320 A | 5/1995 | North et al. | 5,858,007 A | 1/1999 | Fagan et al. |
| 5,417,668 A | 5/1995 | Setzer et al. | 5,865,721 A | 2/1999 | Andrews et al. |
| 5,419,340 A | 5/1995 | Stevens | 5,879,333 A | 3/1999 | Smith et al. |
| 5,423,762 A | 6/1995 | Hillstead | 5,885,217 A | 3/1999 | Gisselberg et al. |
| 5,429,616 A | 7/1995 | Schaffer | 5,895,376 A | 4/1999 | Schwartz et al. |
| 5,437,645 A | 8/1995 | Urban et al. | 5,897,533 A | 4/1999 | Glickman |
| 5,441,504 A | 8/1995 | Pohndorf et al. | 5,911,710 A | 6/1999 | Barry et al. |
| 5,445,613 A | 8/1995 | Orth | 5,916,194 A | 6/1999 | Jacobsen et al. |
| 5,453,095 A | 9/1995 | Davila et al. | 5,919,160 A | 7/1999 | Sanfilippo, II |
| 5,454,409 A | 10/1995 | McAffer et al. | 5,921,968 A | 7/1999 | Lampropoulos et al. |
| 5,460,616 A | 10/1995 | Weinstein et al. | 5,935,112 A | 8/1999 | Stevens et al. |
| 5,472,417 A | 12/1995 | Martin et al. | 5,944,695 A | 8/1999 | Johnson et al. |
| 5,472,418 A | 12/1995 | Palestrant | 5,944,732 A | 8/1999 | Raulerson et al. |
| 5,472,432 A | 12/1995 | Martin | 5,947,953 A | 9/1999 | Ash et al. |
| 5,472,435 A | 12/1995 | Sutton | 5,951,518 A | 9/1999 | Licata et al. |
| 5,474,099 A | 12/1995 | Boehmer et al. | 5,957,912 A | 9/1999 | Heitzmann |
| 5,474,540 A | 12/1995 | Miller et al. | 5,961,485 A | 10/1999 | Martin |
| 5,480,380 A | 1/1996 | Martin | 5,961,486 A | 10/1999 | Twardowski et al. |
| 5,484,401 A | 1/1996 | Rodriguez et al. | 5,967,490 A | 10/1999 | Pike |
| 5,486,159 A | 1/1996 | Mahurkar | 5,971,958 A | 10/1999 | Zhang |
| 5,488,960 A | 2/1996 | Toner | 5,976,103 A | 11/1999 | Martin |
| 5,496,299 A | 3/1996 | Felix et al. | 5,989,213 A | 11/1999 | Maginot |
| 5,496,346 A | 3/1996 | Horzewski et al. | 5,997,486 A | 12/1999 | Burek et al. |
| 5,501,676 A | 3/1996 | Niedospial et al. | 6,001,079 A | 12/1999 | Pourchez |
| 5,507,733 A | 4/1996 | Larkin et al. | 6,024,729 A | 2/2000 | Dehdashtian et al. |
| 5,509,897 A | 4/1996 | Twardowski et al. | 6,027,480 A | 2/2000 | Davis et al. |
| 5,509,902 A | 4/1996 | Raulerson | 6,033,375 A | 3/2000 | Brumbach |
| 5,514,117 A | 5/1996 | Lynn | 6,033,388 A | 3/2000 | Nordstrom et al. |
| 5,520,655 A | 5/1996 | Davila et al. | 6,036,171 A | 3/2000 | Weinheimer et al. |

| | | | | | | |
|---|---|---|---|---|---|---|
| 6,053,904 | A | 4/2000 | Scribner et al. | 6,722,705 B2 | 4/2004 | Korkor |
| 6,068,011 | A | 5/2000 | Paradis | 6,827,710 B1 | 12/2004 | Mooney et al. |
| 6,074,374 | A | 6/2000 | Fulton | 6,843,513 B2 | 1/2005 | Guala |
| 6,074,377 | A | 6/2000 | Sanfilippo, II | 6,872,198 B1 | 3/2005 | Wilson et al. |
| 6,074,379 | A | 6/2000 | Prichard | 6,881,211 B2 | 4/2005 | Schweikert et al. |
| 6,083,207 | A | 7/2000 | Heck | D505,202 S | 5/2005 | Chesnin |
| 6,086,555 | A | 7/2000 | Eliasen et al. | 6,887,220 B2 | 5/2005 | Hogendijk |
| 6,086,570 | A | 7/2000 | Aboul-Hosn et al. | 6,893,056 B2 | 5/2005 | Guala |
| 6,088,889 | A | 7/2000 | Luther et al. | 6,916,051 B2 | 7/2005 | Fisher |
| 6,090,083 | A | 7/2000 | Sell et al. | 6,916,313 B2 | 7/2005 | Cunningham |
| 6,093,154 | A | 7/2000 | Burek et al. | 6,921,396 B1 | 7/2005 | Wilson et al. |
| 6,096,011 | A | 8/2000 | Trombley, III et al. | 6,932,795 B2 | 8/2005 | Lopez et al. |
| 6,099,519 | A | 8/2000 | Olsen et al. | 6,969,381 B2 | 11/2005 | Voorhees |
| 6,106,503 | A | 8/2000 | Pfeiderer et al. | 6,971,390 B1 | 12/2005 | Vasek et al. |
| 6,106,540 | A | 8/2000 | White et al. | 7,044,441 B2 | 5/2006 | Doyle |
| 6,120,476 | A | 9/2000 | Fung et al. | 7,048,724 B2 | 5/2006 | Grossman et al. |
| 6,120,480 | A | 9/2000 | Zhang et al. | 7,094,218 B2 | 8/2006 | Rome et al. |
| 6,132,407 | A | 10/2000 | Genese et al. | 7,163,531 B2 | 1/2007 | Seese et al. |
| 6,142,981 | A | 11/2000 | Heck et al. | 7,182,746 B2 | 2/2007 | Haarala et al. |
| 6,155,610 | A | 12/2000 | Godeau et al. | 7,258,685 B2 | 8/2007 | Kerr |
| 6,156,016 | A | 12/2000 | Maginot | 7,300,430 B2 | 11/2007 | Wilson et al. |
| 6,159,198 | A | 12/2000 | Gardeski et al. | 7,347,853 B2 | 3/2008 | DiFiore et al. |
| 6,162,196 | A | 12/2000 | Hart et al. | 7,377,915 B2 | 5/2008 | Rasmussen et al. |
| 6,171,281 | B1 | 1/2001 | Zhang | 7,470,261 B2 | 12/2008 | Lynn |
| 6,179,806 | B1 | 1/2001 | Sansoucy | 7,578,803 B2 | 8/2009 | Rome et al. |
| 6,190,349 | B1 | 2/2001 | Ash et al. | 7,594,910 B2 | 9/2009 | Butts et al. |
| 6,190,352 | B1 | 2/2001 | Haarala et al. | 7,594,911 B2 | 9/2009 | Powers et al. |
| 6,190,371 | B1 | 2/2001 | Maginot et al. | 8,177,770 B2 | 5/2012 | Rasmussen et al. |
| 6,206,849 | B1 | 3/2001 | Martin et al. | 8,177,771 B2 | 5/2012 | Butts et al. |
| 6,210,366 | B1 | 4/2001 | Sanfilippo, II | 8,206,376 B2 | 6/2012 | Barron et al. |
| 6,213,988 | B1 | 4/2001 | McIvor et al. | 2001/0041857 A1 | 11/2001 | Sansoucy |
| 6,221,057 | B1 | 4/2001 | Schwartz et al. | 2001/0041873 A1 | 11/2001 | Dopper et al. |
| 6,228,060 | B1 | 5/2001 | Howell | 2002/0010437 A1 | 1/2002 | Lopez et al. |
| 6,228,062 | B1 | 5/2001 | Howell et al. | 2002/0077605 A1 | 6/2002 | Fentis et al. |
| 6,258,058 | B1 | 7/2001 | Sanfilippo, II | 2002/0099326 A1 | 7/2002 | Wilson et al. |
| 6,273,871 | B1 | 8/2001 | Davis et al. | 2002/0099327 A1 | 7/2002 | Wilson et al. |
| 6,276,661 | B1 | 8/2001 | Laird | 2002/0128604 A1 | 9/2002 | Nakajima |
| 6,293,927 | B1 | 9/2001 | McGuckin, Jr. | 2002/0147431 A1 | 10/2002 | Lopez et al. |
| 6,322,541 | B2 | 11/2001 | West et al. | 2003/0065288 A1 | 4/2003 | Brimhall et al. |
| 6,331,176 | B1 | 12/2001 | Becker et al. | 2003/0066218 A1 | 4/2003 | Schweikert |
| 6,332,874 | B1 | 12/2001 | Eliasen et al. | 2003/0088213 A1 | 5/2003 | Schweikert et al. |
| 6,338,725 | B1 | 1/2002 | Hermann et al. | 2003/0153898 A1 | 8/2003 | Schon et al. |
| 6,344,033 | B1 | 2/2002 | Jepson et al. | 2003/0187411 A1 | 10/2003 | Constantz |
| 6,352,520 | B1 | 3/2002 | Miyazaki et al. | 2003/0199853 A1 | 10/2003 | Olsen et al. |
| 6,402,723 | B1 | 6/2002 | Lampropoulos et al. | 2003/0201639 A1 | 10/2003 | Korkor |
| 6,413,250 | B1 | 7/2002 | Smith et al. | 2003/0225379 A1 | 12/2003 | Schaffer et al. |
| 6,423,050 | B1 | 7/2002 | Twardowski | 2004/0065333 A1 | 4/2004 | Wilson et al. |
| 6,423,053 | B1 | 7/2002 | Lee | 2004/0082923 A1 | 4/2004 | Field |
| 6,454,744 | B1 | 9/2002 | Spohn et al. | 2004/0092863 A1 | 5/2004 | Raulerson et al. |
| 6,458,103 | B1 | 10/2002 | Albert et al. | 2004/0097903 A1 | 5/2004 | Raulerson |
| 6,494,860 | B2 | 12/2002 | Rocamora et al. | 2004/0122418 A1 | 6/2004 | Voorhees |
| 6,497,681 | B1 | 12/2002 | Brenner | 2004/0158208 A1 | 8/2004 | Hiejima |
| 6,508,790 | B1 | 1/2003 | Lawrence | 2004/0167463 A1 | 8/2004 | Zawacki et al. |
| 6,508,807 | B1 | 1/2003 | Peters | 2004/0167478 A1 | 8/2004 | Mooney et al. |
| 6,520,939 | B2 | 2/2003 | Lafontaine | 2004/0171997 A1 | 9/2004 | Wilson et al. |
| 6,544,247 | B1 | 4/2003 | Gardeski et al. | 2004/0172003 A1 | 9/2004 | Wilson et al. |
| 6,551,283 | B1 | 4/2003 | Guo et al. | 2004/0176739 A1 | 9/2004 | Stephens et al. |
| 6,562,023 | B1 | 5/2003 | Marrs et al. | 2004/0183305 A1 | 9/2004 | Fisher |
| 6,575,960 | B2 | 6/2003 | Becker et al. | 2004/0186444 A1 | 9/2004 | Daly et al. |
| 6,589,262 | B1 | 7/2003 | Honebrink et al. | 2004/0186445 A1 | 9/2004 | Raulerson et al. |
| 6,592,544 | B1 | 7/2003 | Mooney et al. | 2004/0193119 A1 | 9/2004 | Canaud et al. |
| 6,592,558 | B2 | 7/2003 | Quah et al. | 2004/0243095 A1 | 12/2004 | Nimkar et al. |
| 6,592,565 | B2 | 7/2003 | Twardowski | 2005/0049555 A1 | 3/2005 | Moorehead et al. |
| 6,623,460 | B1 | 9/2003 | Heck | 2005/0080398 A1 | 4/2005 | Markel et al. |
| 6,626,418 | B2 | 9/2003 | Kiehne et al. | 2005/0085765 A1 | 4/2005 | Voorhees |
| 6,629,350 | B2 | 10/2003 | Motsenbocker | 2005/0085794 A1 | 4/2005 | Denoth et al. |
| 6,632,200 | B2 | 10/2003 | Guo et al. | 2005/0095891 A1 | 5/2005 | Schorn |
| 6,638,242 | B2 | 10/2003 | Wilson et al. | 2005/0096585 A1 | 5/2005 | Schon et al. |
| 6,641,574 | B2 | 11/2003 | Badia Segura et al. | 2005/0113805 A1 | 5/2005 | Devellian et al. |
| 6,645,178 | B1 | 11/2003 | Junker et al. | 2005/0187535 A1 | 8/2005 | Wilson et al. |
| 6,663,595 | B2 | 12/2003 | Spohn et al. | 2005/0209572 A1 | 9/2005 | Rome et al. |
| 6,669,681 | B2 | 12/2003 | Jepson et al. | 2005/0209581 A1 | 9/2005 | Butts et al. |
| 6,682,498 | B2 | 1/2004 | Ross | 2005/0209584 A1 | 9/2005 | Rome |
| 6,682,519 | B1 | 1/2004 | Schon | 2005/0256461 A1 | 11/2005 | DiFiore et al. |
| 6,689,109 | B2 | 2/2004 | Lynn | 2005/0261636 A1 | 11/2005 | Rome et al. |
| 6,692,464 | B2 | 2/2004 | Graf | 2005/0261664 A1 | 11/2005 | Rome et al. |
| 6,695,832 | B2 | 2/2004 | Schon et al. | 2005/0261665 A1 | 11/2005 | Voorhees |
| 6,712,796 | B2 | 3/2004 | Fentis et al. | 2006/0015074 A1 | 1/2006 | Lynn |
| 6,719,749 | B1 | 4/2004 | Schweikert et al. | 2006/0015086 A1 | 1/2006 | Rasmussen et al. |

| | | | |
|---|---|---|---|
| 2006/0084929 | A1 | 4/2006 | Eliasen |
| 2006/0129134 | A1 | 6/2006 | Kerr |
| 2006/0276773 | A1 | 12/2006 | Wilson et al. |
| 2007/0016167 | A1 | 1/2007 | Smith et al. |
| 2007/0060866 | A1 | 3/2007 | Raulerson et al. |
| 2008/0009832 | A1 | 1/2008 | Barron et al. |
| 2008/0200901 | A1 | 8/2008 | Rasmussen et al. |
| 2009/0013944 | A1 | 1/2009 | Re Fiorentin et al. |
| 2009/0137944 | A1 | 5/2009 | Haarala et al. |
| 2010/0010445 | A1 | 1/2010 | Powers et al. |
| 2010/0016838 | A1 | 1/2010 | Butts et al. |

FOREIGN PATENT DOCUMENTS

| | | |
|---|---|---|
| EP | 0439263 A1 | 7/1991 |
| EP | 0616817 A1 | 9/1994 |
| WO | 8401902 A1 | 5/1984 |
| WO | 9722374 A1 | 6/1997 |
| WO | 0023137 A1 | 4/2000 |
| WO | 02058776 A2 | 8/2002 |
| WO | 03030960 A2 | 4/2003 |
| WO | 03030962 A2 | 4/2003 |
| WO | 03033049 A2 | 4/2003 |
| WO | 2006004943 A2 | 1/2006 |
| WO | 2006066023 A2 | 6/2006 |
| WO | 2006130133 A1 | 12/2006 |
| WO | 2006130166 A2 | 12/2006 |

OTHER PUBLICATIONS

PCT/US2010/040084 filed Jun. 25, 2010 Written Opinion dated Sep. 27, 2010.
Arrow® Cannon™ II Plus Product Brochure, Feb. 2012.
Camp, "Care of the Groshong Catheter", Oncol Nurs Forum, vol. 15, No. 6, 1988.
Delmore et al., "Experience with the Groshong Long-Term Central Venous Catheter", Gynecologic Oncology 34, 216-218 (1989).
Goldfarb et al., "Chronic Venous Access Bedside Placement Technique and Complications," Cancer Practice vol. 2, No. 4, pp. 279-283 (Jul./Aug. 1994).
Health Devices, "Hazard Report," vol. 25, Nos. 5-6, pp. 214-215, May-Jun. 1996.
Hull et al., "The Groshong Catheter: Initial Experience and Early Results of Imging-guided Placement," Cardiovascular Radiology 185:803-807 (1992).
Malviya et al., "Vascular Access in Gynecological Cancer Using the Groshong Right Atrial Catheter", Gynecological Oncology 33, 313-316 (1989).
PCT/US2005/009150 filed Mar. 18, 2005 Preliminary Report on Patentability dated May 26, 2006.
PCT/US2005/009150 filed Mar. 18, 2005 Search Report dated Jun. 7, 2005.
PCT/US2005/009150 filed Mar. 18, 2005 Written Opinion dated Jun. 17, 2005.
Salem et al., "A New Peripherally Implanted Subcutaneous Permanent Central Venous Access Device for Patients Requiring Chemotherapy," Journal of Clinical Oncology, vol. 11, No. 11, p. 2181-2185 (Nov. 1993).
Twardowski et al., "Measuring Central Venous Structures in Humans: Implications for Central-Vein Catheter Dimensions," The Journal of Vascular Access 3:21-37 (2002).
U.S. Appl. No. 10/803,207, filed Mar. 18, 2004 Non-Final Office Action dated Sep. 19, 2005.
U.S. Appl. No. 10/803,207, filed Mar. 18, 2004 Notice of Allowance dated Apr. 21, 2006.
U.S. Appl. No. 10/803,279, filed Mar. 18, 2004 Advisory Action dated Aug. 22, 2007.
U.S. Appl. No. 10/803,279, filed Mar. 18, 2004 Final Office Action dated May 31, 2007.
U.S. Appl. No. 10/803,279, filed Mar. 18, 2004 Final Office Action dated Oct. 1, 2008.
U.S. Appl. No. 10/803,279, filed Mar. 18, 2004 Non-Final Office Action dated Apr. 2, 2009.
U.S. Appl. No. 10/803,279, filed Mar. 18, 2004 Non-Final Office Action dated Jun. 5, 2006.
U.S. Appl. No. 10/803,279, filed Mar. 18, 2004 Non-Final Office Action dated Sep. 20, 2007.
U.S. Appl. No. 10/803,279, filed Mar. 18, 2004 Non-Final Office Action dated Dec. 1, 2006.
U.S. Appl. No. 10/803,279, filed Mar. 18, 2004 Notice of Allowance dated May 28, 2009.
U.S. Appl. No. 10/803,512, filed Mar. 18, 2004 Advisory Action dated Oct. 16, 2008.
U.S. Appl. No. 10/803,512, filed Mar. 18, 2004 Final Office Action dated May 30, 2008.
U.S. Appl. No. 10/803,512, filed Mar. 18, 2004 Non-Final Office Action dated Jan. 24, 2008.
U.S. Appl. No. 10/803,512, filed Mar. 18, 2004 Non-Final Office Action dated May 24, 2010.
U.S. Appl. No. 10/803,512, filed Mar. 18, 2004 Non-Final Office Action dated Jul. 22, 2009.
U.S. Appl. No. 10/803,512, filed Mar. 18, 2004 Final Office Action dated Sep. 28, 2010.
U.S. Appl. No. 10/803,513, filed Mar. 18, 2004 Non-Final Office Action dated Jul. 25, 2008.
U.S. Appl. No. 10/803,513, filed Mar. 18, 2004 Notice of Allowance dated Jun. 12, 2009.
U.S. Appl. No. 11/076,564, filed Mar. 8, 2005 Advisory Action dated Nov. 16, 2006.
U.S. Appl. No. 11/076,564, filed Mar. 8, 2005 Final Office Action dated Jul. 27, 2007.
U.S. Appl. No. 11/076,564, filed Mar. 8, 2005 Final Office Action dated Aug. 25, 2006.
U.S. Appl. No. 11/076,564, filed Mar. 8, 2005 Non-Final Office Action dated Jan. 23, 2008.
U.S. Appl. No. 11/076,564, filed Mar. 8, 2005 Non-Final Office Action dated Feb. 9, 2007.
U.S. Appl. No. 11/076,564, filed Mar. 8, 2005 Non-Final Office Action dated Mar. 9, 2006.
U.S. Appl. No. 11/076,564, filed Mar. 8, 2005 Non-Final Office Action dated Dec. 17, 2008.
U.S. Appl. No. 11/076,564, filed Mar. 8, 2005 Notice of Allowance dated Jun. 17, 2009.
U.S. Appl. No. 11/096,553, filed Apr. 1, 2005 Advisory Action dated Aug. 1, 2007.
U.S. Appl. No. 11/096,553, filed Apr. 1, 2005 Final Office Action dated Feb. 27, 2007.
U.S. Appl. No. 11/096,553, filed Apr. 1, 2005 Non-Final Office Action dated Jan. 24, 2006.
U.S. Appl. No. 11/096,553, filed Apr. 1, 2005 Non-Final Office Action dated May 19, 2006.
U.S. Appl. No. 11/096,553, filed Apr. 1, 2005 Non-Final Office Action dated Oct. 10, 2007.
U.S. Appl. No. 11/096,553, filed Apr. 1, 2005 Notice of Allowance dated Mar. 25, 2008.
U.S. Appl. No. 11/122,303, filed May 3, 2005 Advisory Action dated Jul. 14, 2008.
U.S. Appl. No. 11/122,303, filed May 3, 2005 Final Office Action dated Apr. 30, 2008.
U.S. Appl. No. 11/122,303, filed May 3, 2005 Non-Final Office Action dated Jan. 20, 2010.
U.S. Appl. No. 11/122,303, filed May 3, 2005 Non-Final Office Action dated Jun. 8, 2009.
U.S. Appl. No. 11/122,303, filed May 3, 2005 Non-Final Office Action dated Sep. 13, 2007.
U.S. Appl. No. 11/122,303, filed May 3, 2005 Notice of Allowance dated Jul. 9, 2010.
U.S. Appl. No. 11/122,303, filed May 3, 2005 Notice of Allowance dated Sep. 2, 2010.
U.S. Appl. No. 11/471,193, filed Jun. 20, 2006 Non-Final Office Action dated Jan. 14, 2010.
U.S. Appl. No. 11/471,193, filed Jun. 20, 2006 Notice of Allowance dated Jul. 26, 2010.
U.S. Appl. No. 12/106,704, filed Apr. 21, 2008 Final Office Action dated Apr. 15, 2010.
U.S. Appl. No. 12/106,704, filed Apr. 21, 2008 Non-Final Office Action dated Apr. 27, 2009.

U.S. Appl. No. 12/106,704, filed Apr. 21, 2008 Non-Final Office Action dated Oct. 22, 2009.

U.S. Appl. No. 12/563,776, filed Sep. 21, 2009 Non-Final Office Action dated Jun. 16, 2010.

U.S. Appl. No. 12/563,776, filed Sep. 12, 2009 Notice of Allowance dated Nov. 12, 2010.

U.S. Appl. No. 12/563,996, filed Sep. 21, 2009 Final Office Action dated Dec. 1, 2011.

U.S. Appl. No. 12/563,996, filed Sep. 21, 2009 Non-Final Office Action dated Jun. 13, 2011.

Vesely, "Central Venous Catheter Tip Position: A Continuing Controversy," JVIR vol. 14, No. 5, pp. 527-534 (May 2003).

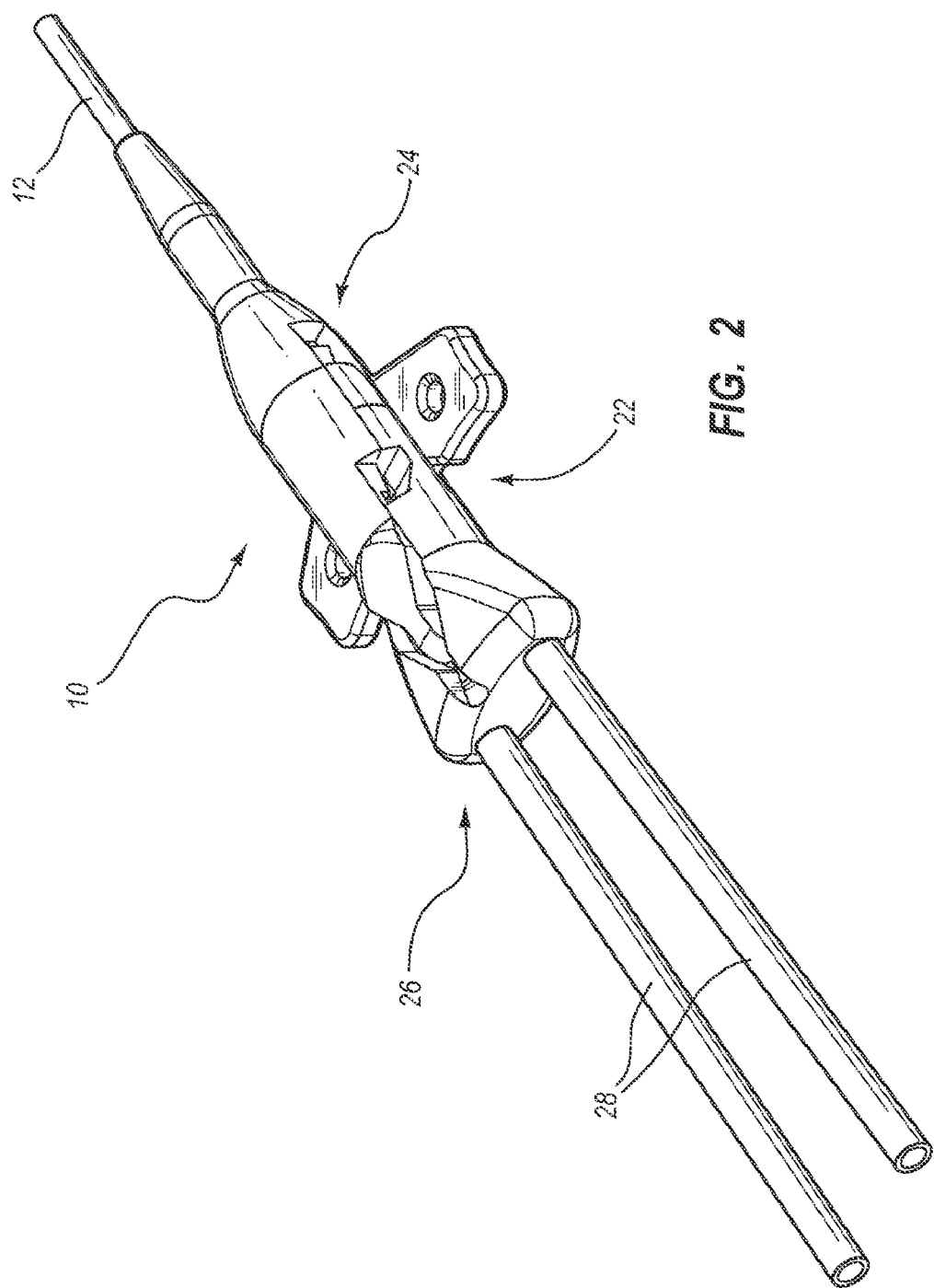

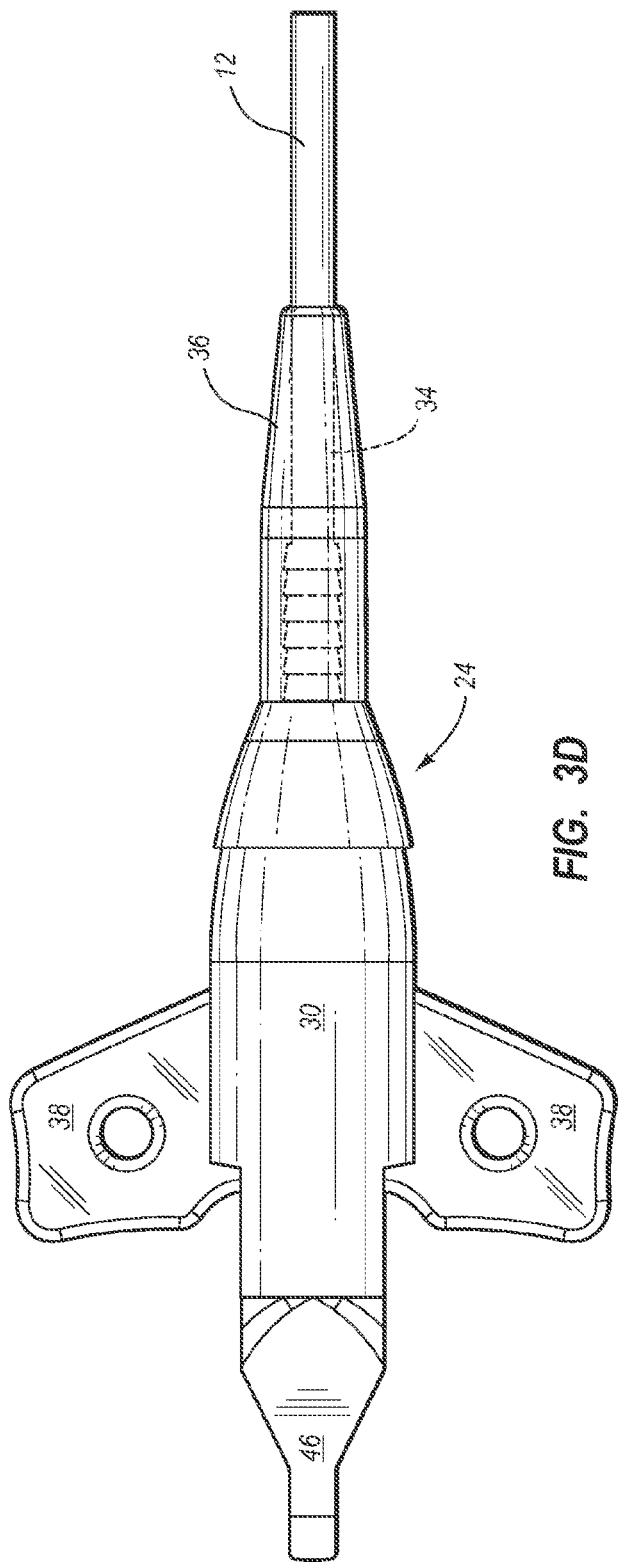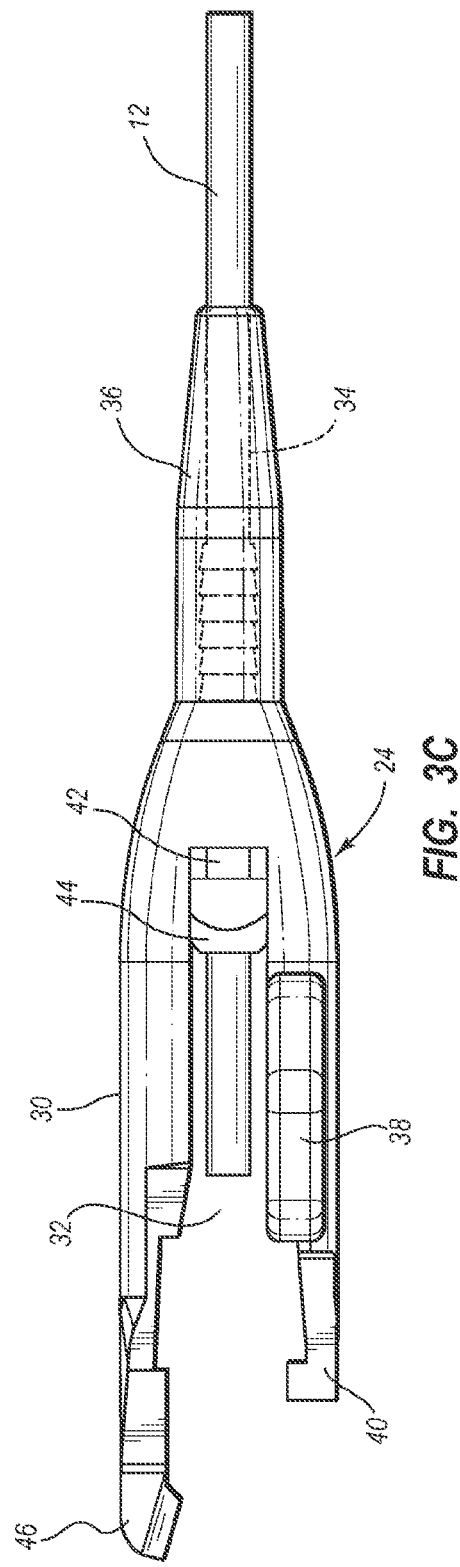
FIG. 3D
FIG. 3C

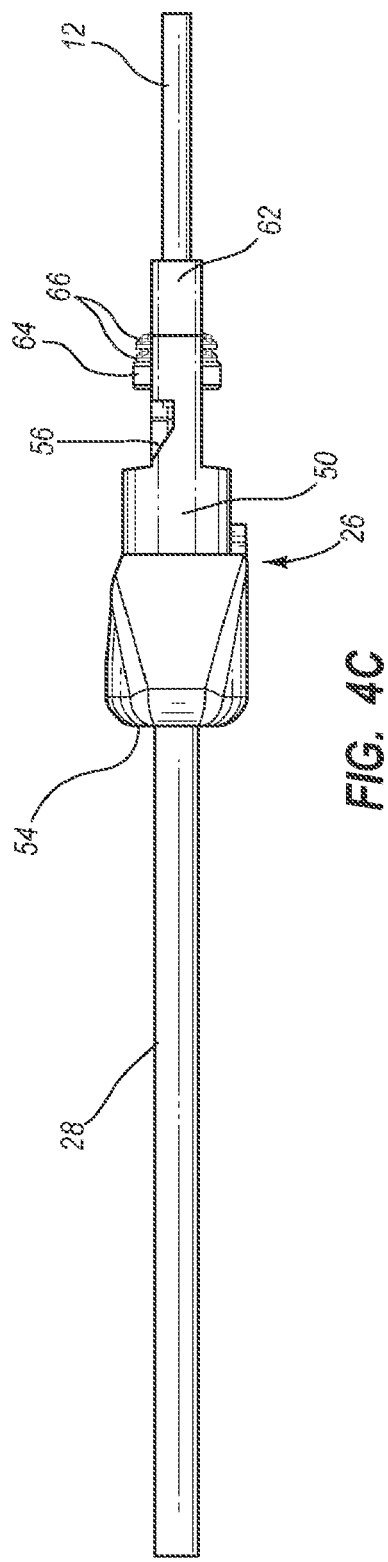
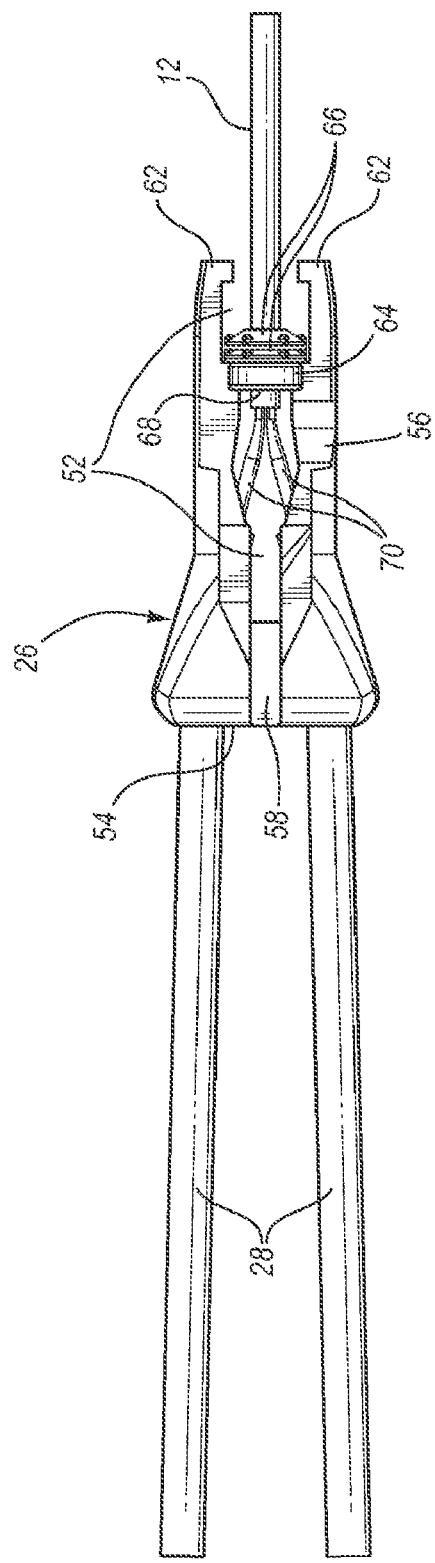

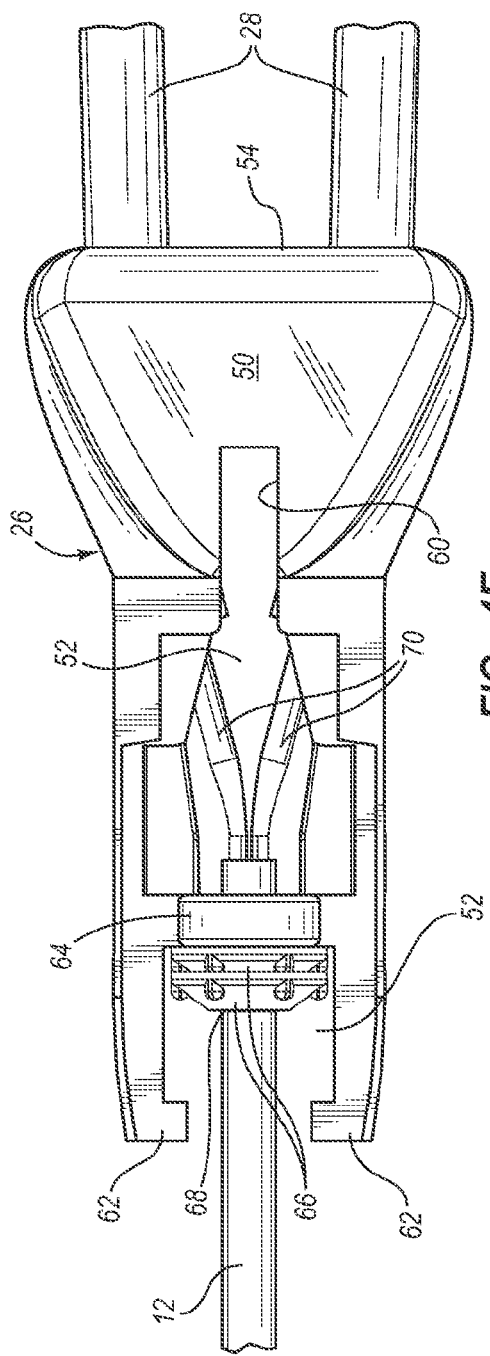
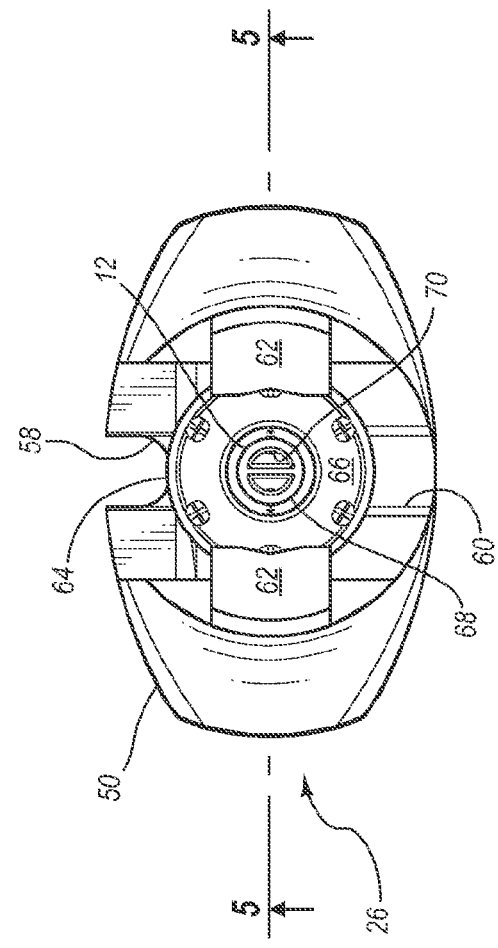
FIG. 4E
FIG. 4F

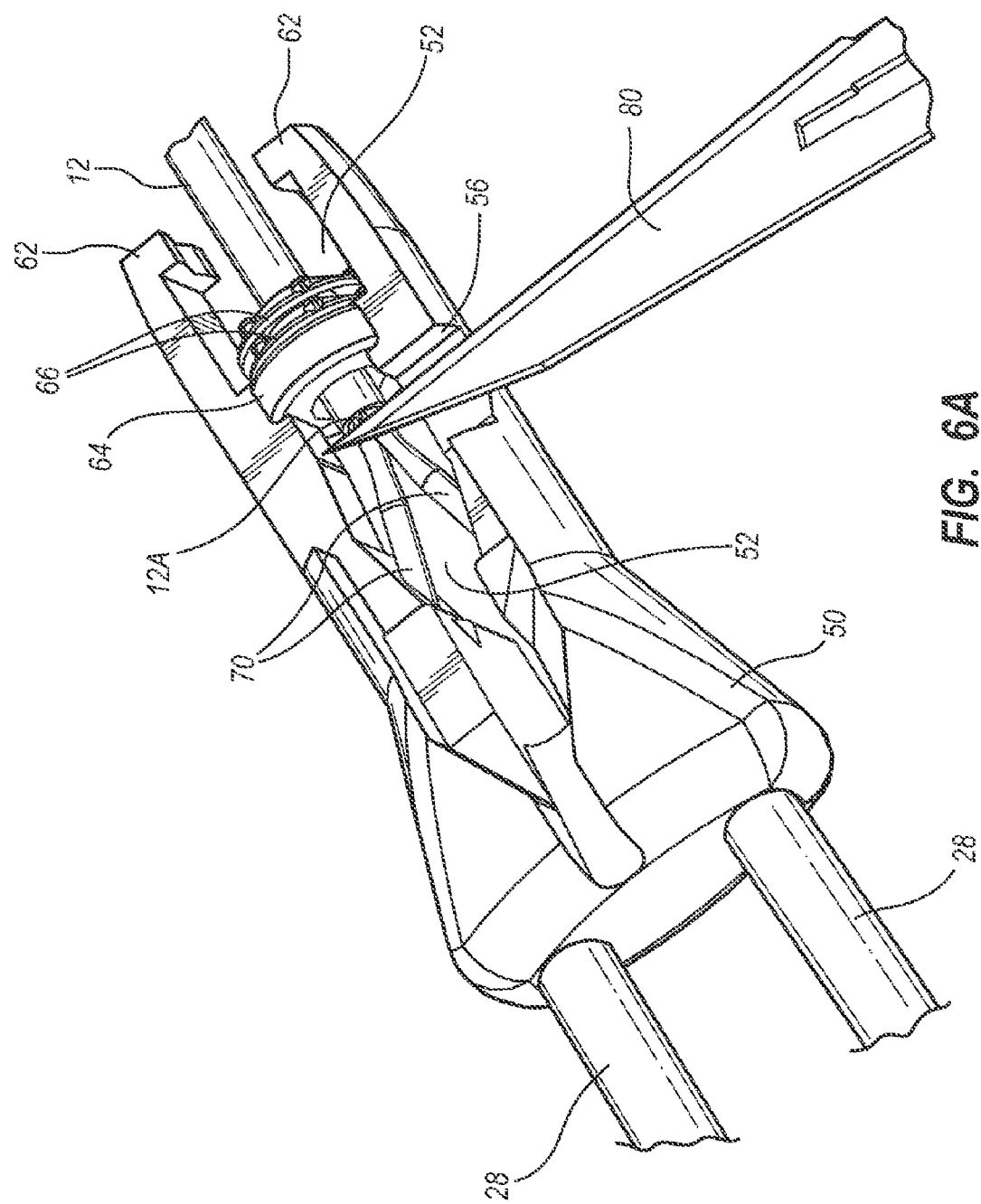

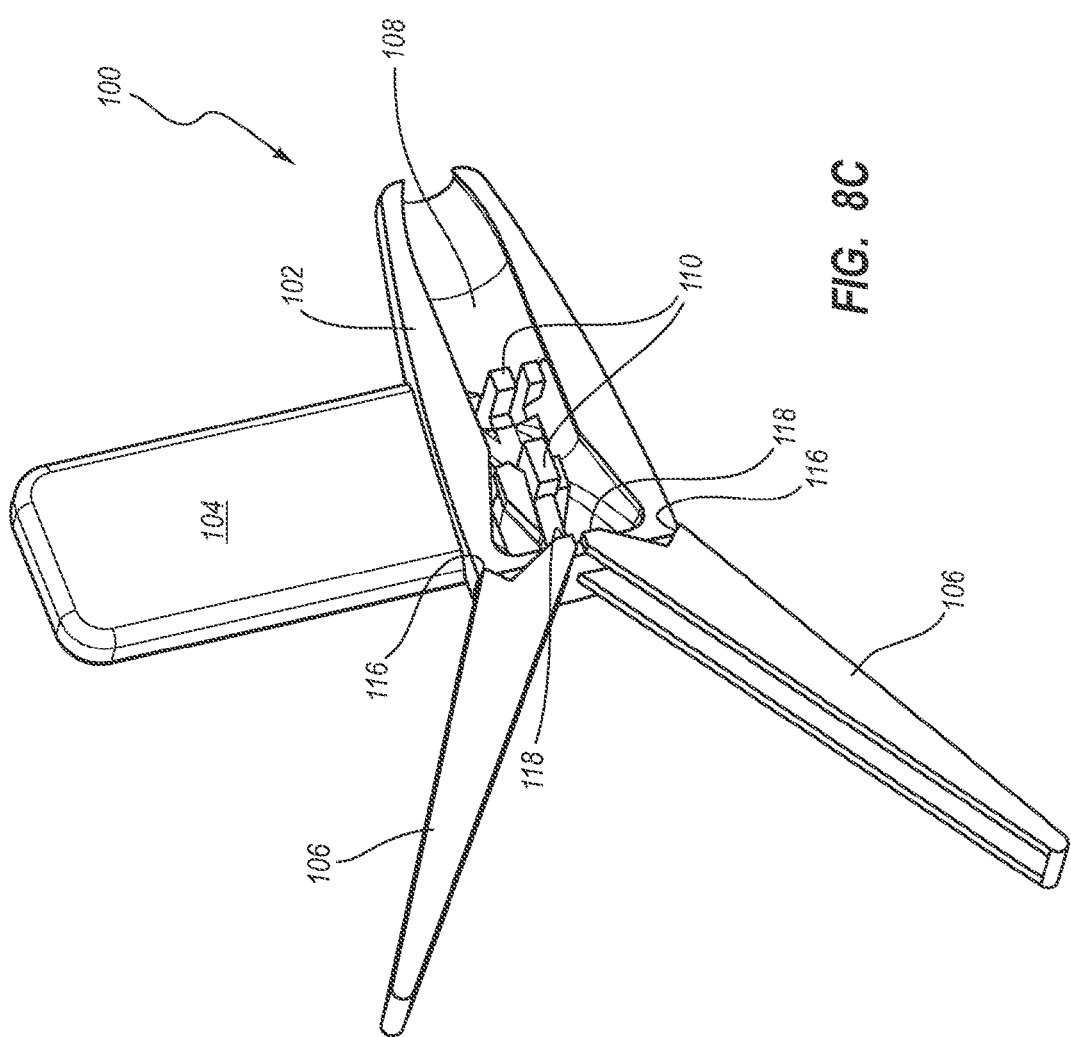

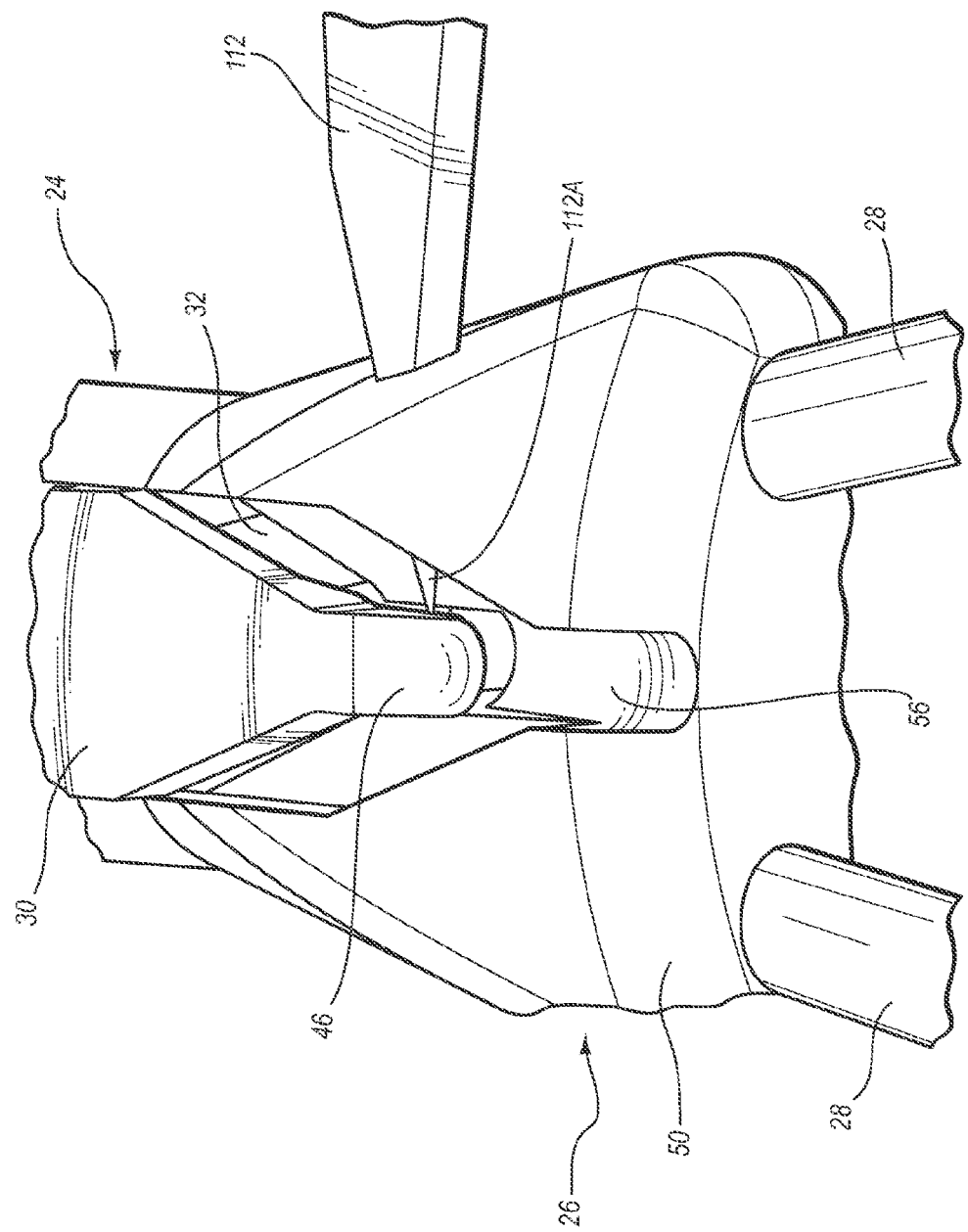

US 8,337,484 B2

PROXIMALLY TRIMMABLE CATHETER INCLUDING PRE-ATTACHED BIFURCATION AND RELATED METHODS

CROSS-REFERENCE TO RELATED APPLICATIONS

This application claims the benefit of U.S. Provisional Patent Application No. 61/220,943, filed Jun. 26, 2009, and entitled "Direct Placement Catheter and Method of Use," which is incorporated herein by reference in its entirety.

BRIEF SUMMARY

Briefly summarized, embodiments of the present invention are directed to a proximally trimmable catheter. In one embodiment, the catheter includes a multi-lumen catheter tube, a set of one or more extension tubes, and a hub for fluidly connecting the two. In a first unlocked state, the hub is axially slidable along the catheter tube. The hub includes one more tube pins that are in fluid communication with the extension tubes.

A cutting member is positioned to longitudinally cut the catheter tube during axial sliding of the hub along the catheter tube such that distal portions of the tube pins remain disposed within the lumens of the uncut portion of the catheter tube distal to the cutting member.

When positioned as desired, the hub can be locked into a second locked state such that it is no longer axially slidable along the catheter tube. The tube pins are fluidly sealed within the lumens of the catheter tube by a compression component or other suitable element as to establish fluid communication between the extension tubes and the lumens of the catheter tube via the tube pins.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 2 is a perspective view of a catheter including a hub in a first unlocked state and configured in accordance with one embodiment;

FIGS. 3A-3F are various views of a distal portion of the hub of FIG. 2;

FIGS. 4A-4F are various views of a proximal portion of the hub of FIG. 2;

FIGS. 6A-6B are various views of a cutting member positioned with respect to the proximal hub portion;

FIGS. 8A-8E are various views of an assembly tool for use with the hub of FIG. 2 according to one embodiment.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1-9D depict embodiments of the present invention, which are generally directed to a proximally trimmable catheter for use in gaining access to a body of a patient, such as access to a patient's vasculature, for instance. The catheter includes a catheter tube defining one or more lumens and a hub. The hub is configured to be distally slid along the length of the catheter tube. So configured, the hub can be positioned as desired along the length of the catheter tube with respect to the insertion site of the catheter. Once positioned as desired, the hub can be locked into position and establish fluid communication between the lumen(s) of the catheter tube and one or more extension legs of the catheter.

Figure 1:
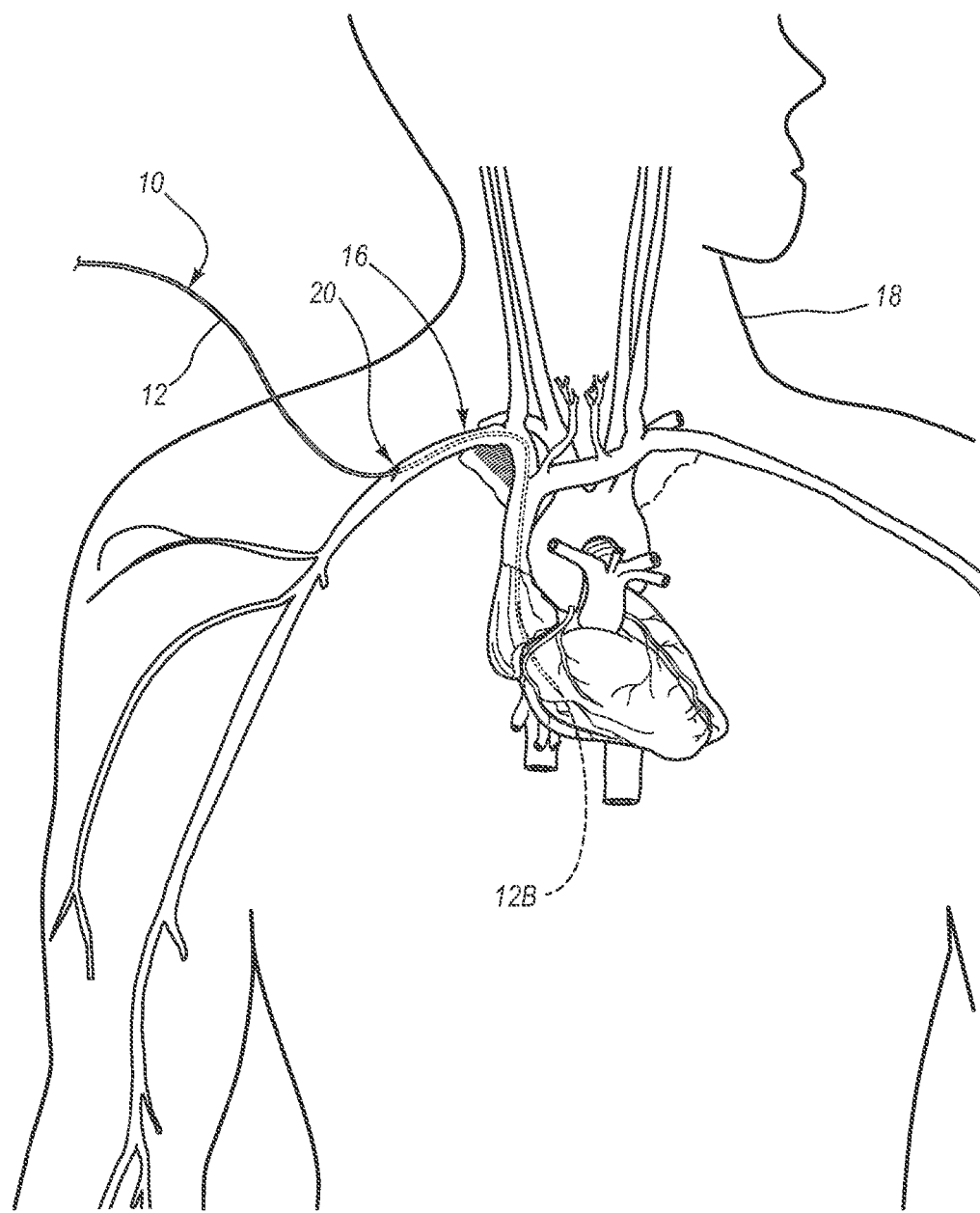
FIG. 1 is a simplified view of a catheter positioned in a body of a patient, showing one possible environment for practice of an embodiment of the present invention.
Figure 3A:
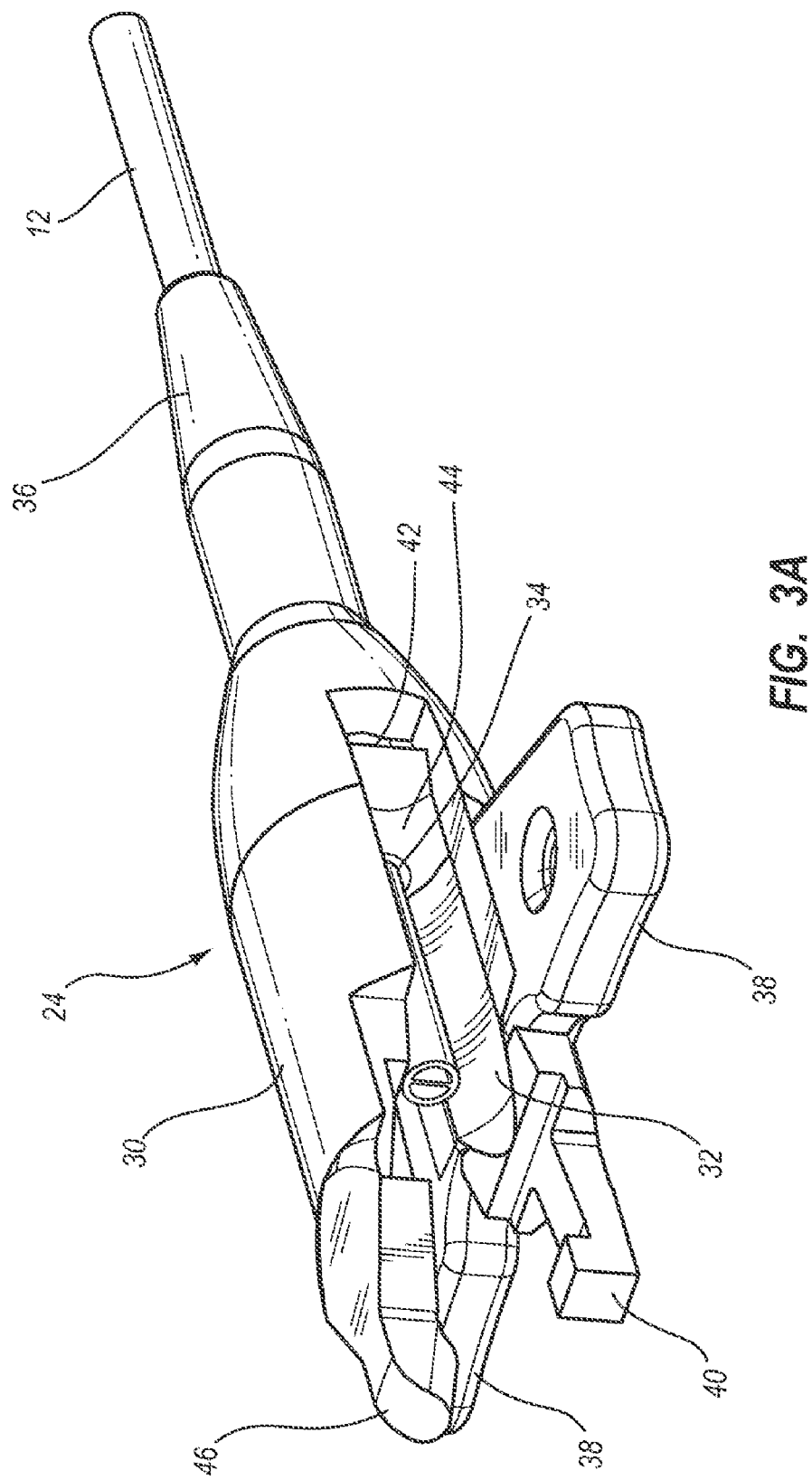
Figure 3B:
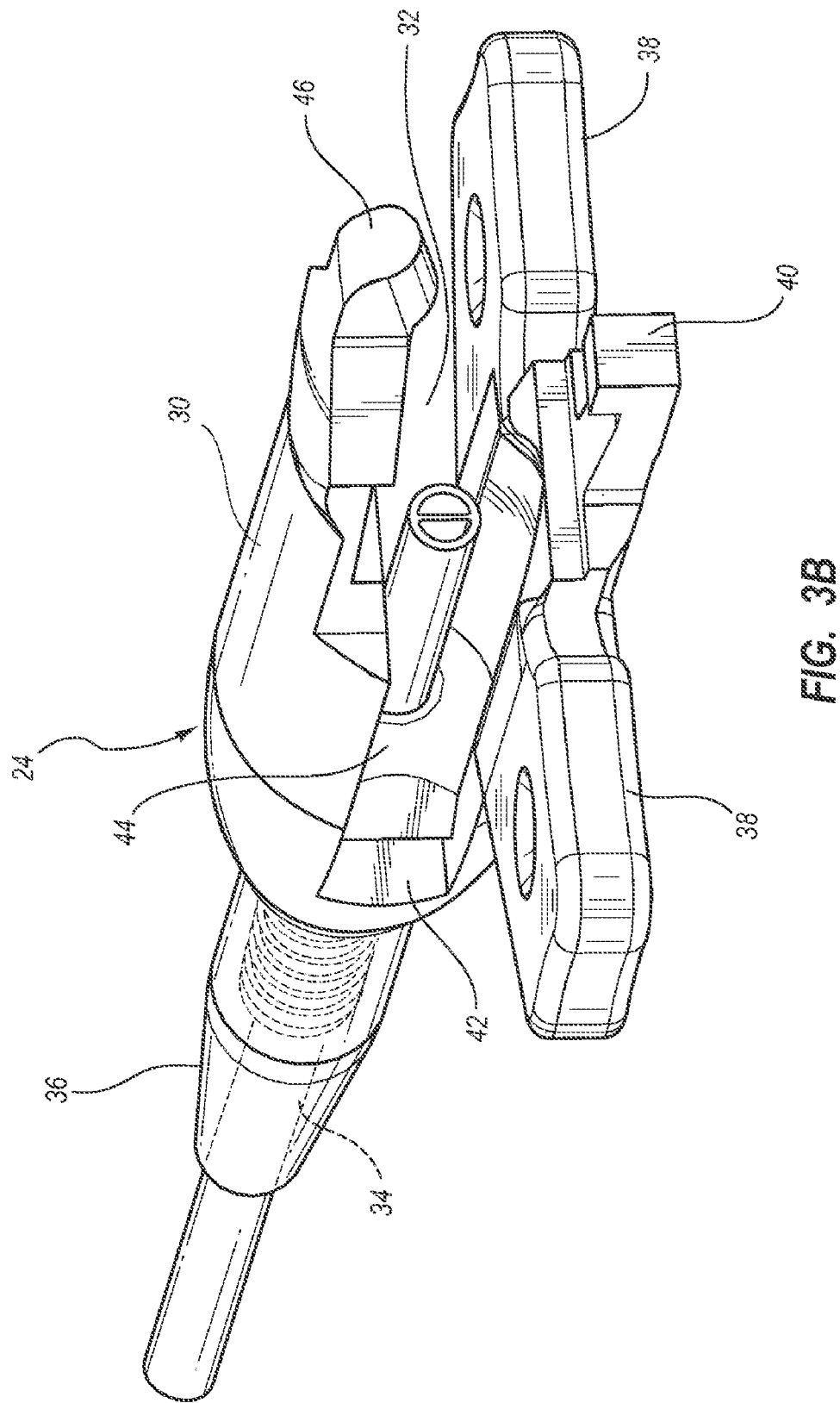
Figure 3E:
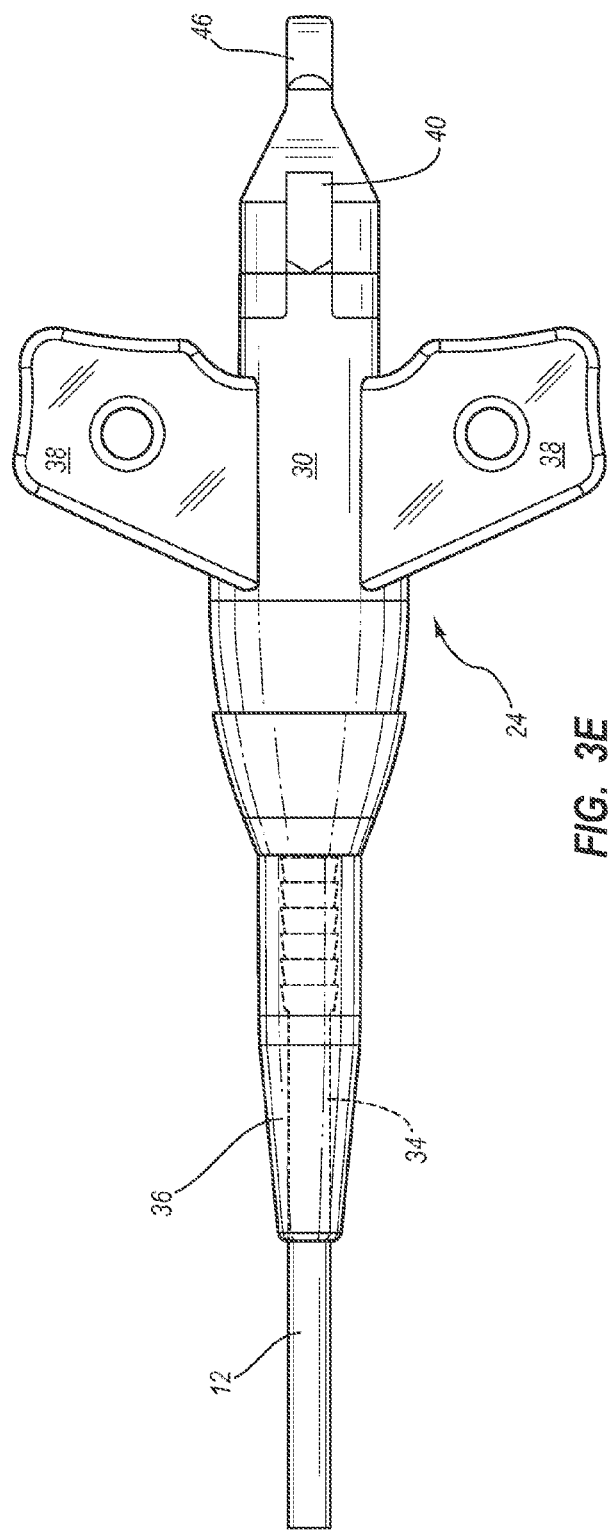
Figure 3F:
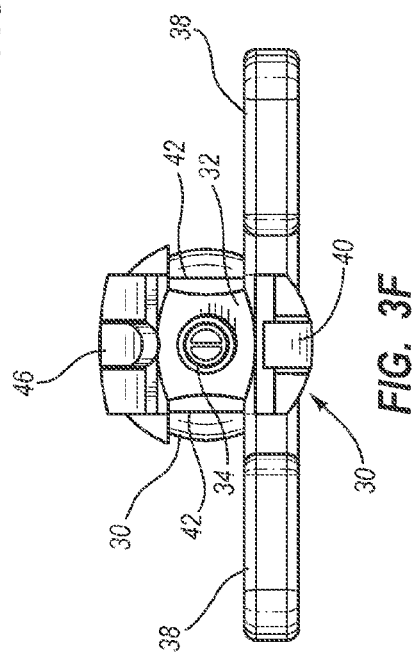
Figure 4A:
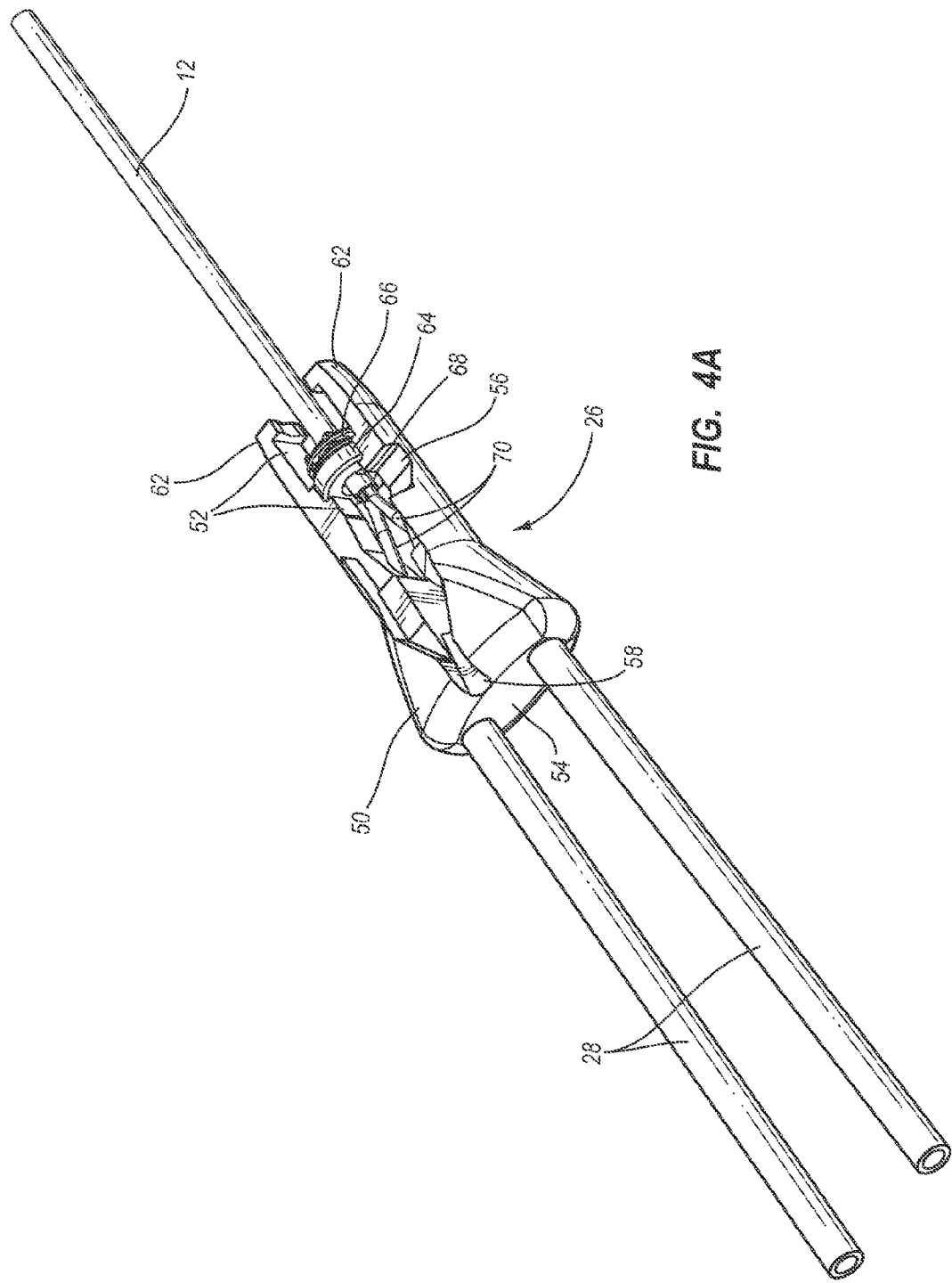
Figure 4B:
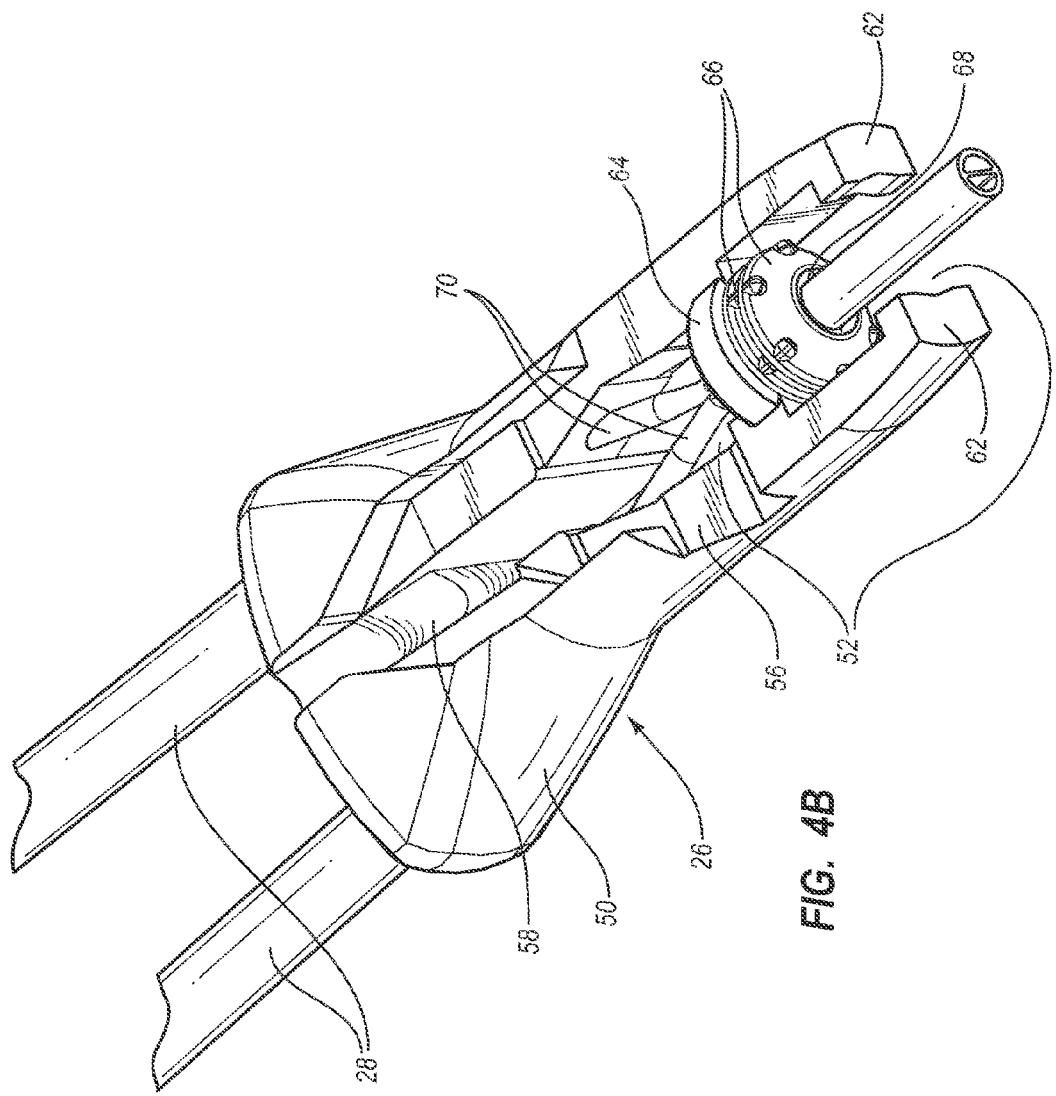

FIG. 1 depicts details of one possible environment in which the present catheter can be employed, in accordance with one example embodiment. In particular, FIG. 1 shows a catheter 10 including a tube 12, a distal portion of which is inserted into a vasculature 16 of a patient 18. Including one or more lumens, the catheter 10 can be advanced through the vasculature in a distal direction from an insertion site 20 to a desired or predetermined destination within the patient's body. In one embodiment, the catheter 10 can include a peripherally inserted central catheter ("PICC"), a central venous catheter ("CVC"), or another suitable catheter or medical device. One possible destination for a distal end 12B of the catheter tube 12 is within the superior vena cava ("SVC"). In other embodiments, the catheter tube can be advanced to other suitable destinations within the patient. It should therefore be appreciated that the above environment is merely one example of possible use; indeed, other catheters and tubular type medical devices for placement in a variety of circumstances can benefit from the principles described herein.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Further, the words "including," "has," and "having," as used herein, including the claims, shall have the same meaning as the word "comprising."

FIG. 2 depicts a perspective view of a hub 22 of the catheter 10, which is configured to enable fluid communication between the one or more lumens of the catheter tube 12 and one or more extension legs 28. The hub 22 is shown in a first unlocked configuration and includes a distal hub portion 24 and a proximal hub portion 26 which lockingly engage one another in a manner to be described further below.

FIGS. 3A-3F show that in the present embodiment the distal hub portion 24 includes a body 30 defining a cavity 32 sized to inter-engage with the proximal hub portion 26. The body 30, together with a nose portion 36 thereof, further defines a conduit 34 through which extends a proximal portion of the catheter tube 12. Suture wings 38 for securing the hub 22 to the body of the patient 18 can also be included.

A connector latch 40 is included for enabling locking attachment of the distal hub portion 24 with the proximal hub portion 26 after placement of the hub 22 is complete, as will be described. Additionally, receptacles 42 are included on the body 30 of the distal hub portion 24 for engagement with corresponding latches 62 (FIG. 4A) included on the proximal hub portion 26. Of course, it is appreciated that the latches and receptacles described herein are merely one example for enabling attachment between the two hub portions 24 and 26; other attachment modes can also be employed without limitation. For example, the use of differing numbers of locking members, the use of differently shaped locking members, and the placement of the locking members in other locations on the distal hub portion are contemplated.

The distal hub portion 24 further includes an actuation surface 44, disposed adjacent the cavity 32 about a proximal opening of the conduit 34, which is configured to activate a compression element for sealing a fluid path of the catheter, as will be described further below. A tip portion 46 also proximally extends from the distal hub portion 24.

FIGS. 4A-4F depict various details of the proximal hub portion 26 of FIG. 2. As shown, the proximal hub portion 26 includes a body 50 that is sized to inter-engage with the proximal hub portion 26. The body 50 of the proximal hub portion 26 defines various features, including a cavity 52 a base surface 54 adjacent the points of entry for the extension legs 28 into the body, and a notch 56 in communication with the cavity. A notch 58 is also defined by the body 50 for receiving the tip portion 46 of the distal hub portion 24 (FIG. 3A) when the distal and proximal hub portions are mated together.

As best seen in FIG. 4E, the proximal hub portion 24 includes a latch receptacle 60 for receiving the connector latch 40 of the distal hub portion 24 when the hub portions are mated to one another. In addition, the proximal hub portion 26 includes two connector latches 62 configured to engage the receptacles 42 included on the distal hub portion 24, best seen in FIGS. 3A and 3B. As has been mentioned, the latches and receptacles described herein serve as one example of structures for lockingly mating the distal hub portion 24 to the proximal hub portion after positioning of the hub (described below) is complete.

Figure 5:
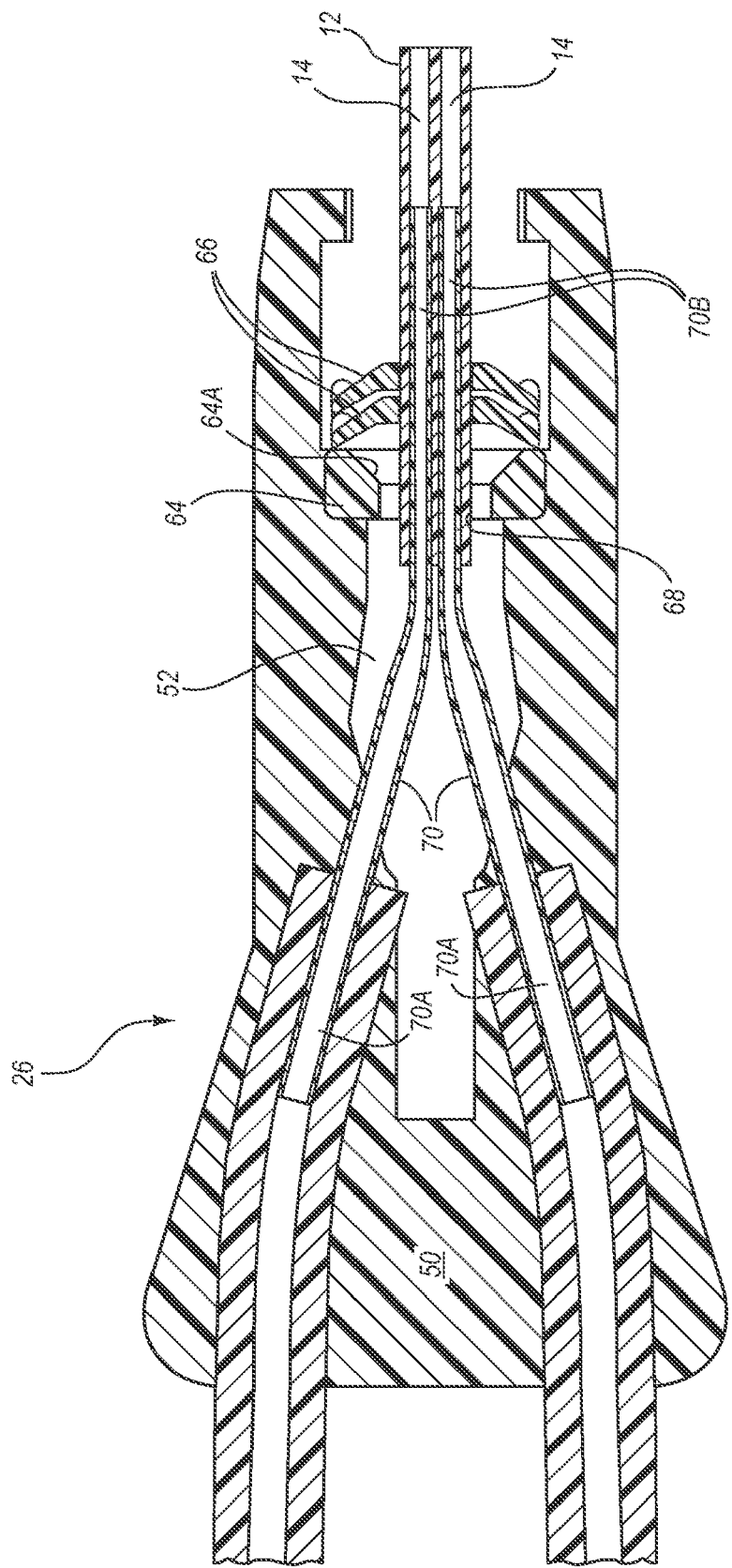
FIG. 5 is a cross sectional view of the proximal hub portion taken along the line 5-5 in FIG. 4F.

As seen in FIGS. 4A-4F, the proximal hub portion 26 includes an annular compression support member 64 disposed in the cavity 52, against which are positioned a plurality of annular compression washers 66. The compression support member 64 and compression washers 66 cooperate to define a conduit 68 through which a proximal portion of the catheter tube 12 extends. In addition, two tube pins 70 are included with the proximal hub portion 26 and each includes a proximal portion 70A and a distal portion 70B. As best seen in FIG. 5, the proximal portion 70A of each tube pin 70 is included within the hub portion body 50 so as to be in fluid communication with a respective one of the extension legs 28. The distal portion 70B of each tube pin 70 is disposed within a respective one of the lumens 14 of the catheter tube 12 via a proximal end 12A thereof. In this way, fluid communication is established between the extension legs 28 and the respective lumens 14 of the catheter tube 12. As will be seen, the compression washers 66 are employed when actuated to seal the interface between the tube pins and the catheter tube 12.

It is appreciated that that the number and type of components for sealing the tube pin/catheter tube interface can vary from what is shown and described herein; indeed, compression rings, collets, barbs, and other sealing components can be employed, for instance. In one embodiment, for instance, a silicone sleeve can be included to seal the tube pin/catheter interface, wherein the sleeve is radially constrained about its outer diameter, then compressed axially so that the inner diameter of the sleeve decreases to seal the interface. Further, note that the number of extension legs, tube pins, and catheter lumens can vary from the dual configurations shown and described herein. For instance, the catheter can include one, three, or more lumens, with a corresponding or different number of tube pins and extension legs.

Figure 6B:
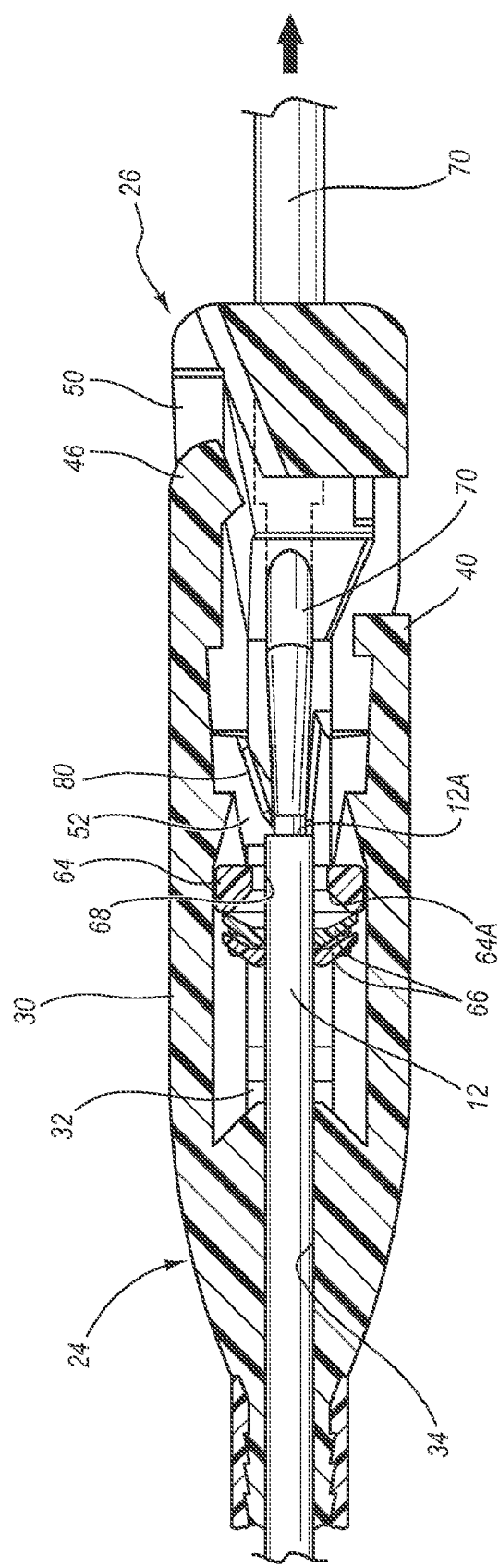

FIGS. 6A and 6B show that in the present embodiment a first cutting member 80 is included to assist in placing the catheter 10. In particular, the first cutting member 80 extends through the notch 56 defined in the body 50 of the proximal hub portion 26 and is positioned to longitudinally slice along the catheter tube 12, cutting across each lumen 14 as the hub 22 is axially slid distally along the catheter tube toward the catheter insertion site 20 of the patient 18 (FIG. 1) during catheter placement procedures, described in greater detail below. Slicing of the catheter tube 12 in this manner enables the distal portion 70B of each tube pin 70 to remain in the uncut portion of its respective catheter tube lumen 14 distal to the first cutting member 80 as the hub is distally advanced along the catheter tube.

FIG. 6B shows that, as the hub 22 advances distally, the catheter tube 12 is cut by the first cutting member 80 and the two resulting pieces of the catheter tube extend proximally through the cavities 32, 52 of the hub portions 24, 26. The first cutting member 80 is shown positioned at a relatively small angle with respect to a longitudinal axis of the catheter tube 12 so as to assist with urging the upper cut portion of the catheter tube to exit the hub portion cavities 32, 52. The cut catheter pieces can be trimmed off after the hub 22 is slid into the desired position with respect to the catheter insertion site 20 of the patient 18. The first cutting member 80 can be included with a removable assembly tool that is temporarily attached to the hub 22, such as that shown in FIG. 8D for instance, or in one embodiment may be integrated into or removable from the hub itself. Thus, it is seen that the first cutting member 80 serves as one example of a means for cutting a proximal portion of the catheter tube; other structures or components can also acceptably accomplish the desired cutting.

Figure 7A:
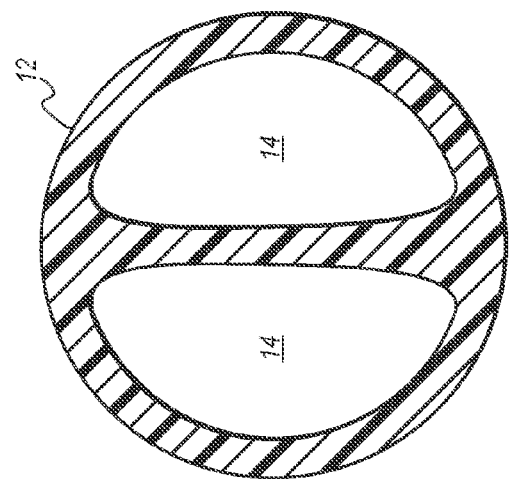
FIGS. 7A-7C are cross sectional views of a catheter showing possible cutting thereof by a cutting member according to one embodiment.
Figure 7B:
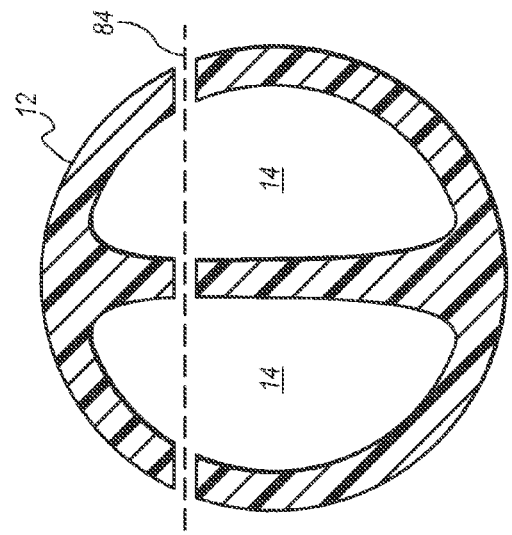
Figure 7C:
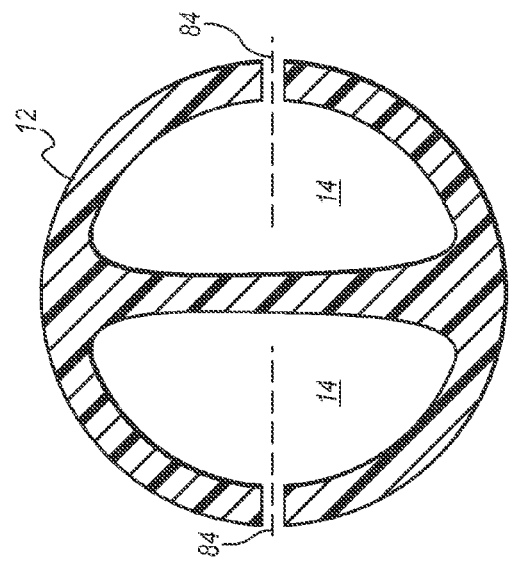

FIG. 7A shows a cross sectional view of the catheter tube 12; FIG. 7B shows the catheter tube after cutting by the first cutting member 80 along a cut line 84 as described above. FIG. 7C shows the catheter tube 12 after cutting along the cut lines 84 by cutting members according to another embodiment, wherein two cutting members cut at opposing points along the outer wall of the catheter. In this example, the catheter tube 12 remains in one piece after cutting, as opposed to the two portions remaining after cutting as shown in FIG. 7B. These and other slicing scenarios are therefore contemplated. For instance, a triple lumen catheter tube can be sliced so as to result in a one, two, or three piece remaining portion after cutting.

FIG. 7C thus illustrates use of another example of a means for cutting a proximal portion of the catheter tube, according to one embodiment. As should therefore appreciated, the number, type, positioning, and other configuration of the means for cutting can vary as appreciated by one skilled in the art.

Reference is now made to FIGS. 8A-8E in describing an assembly tool 100 for assisting in the advancement and locking of the portions of the hub 22 during catheter placement into the body of the patient 18. The assembly tool 100 also maintains the two hub portions 24 and 26 in a state of suitable separation during advancement and positioning of the hub. As shown, the assembly tool 100 includes a main body 102, a cutting member housing 104, and one or more leverage components, here configured as two lever arms 106.

In greater detail, the main body 102 of the assembly tool 100 includes a shell-like structure that defines a cavity 108 sized to receive the two portions 24, 26 of the hub 22 in their engaged but unlocked state as shown in FIG. 2. As best seen in FIG. 8C, the main body 102 further defines various stabilization features 110 included within the cavity 108 to assist in securing the hub 22 in place while it is positioned within the cavity. In one embodiment, one or more stabilization features can be included on the cutting member housing as well.

Figure 8A:
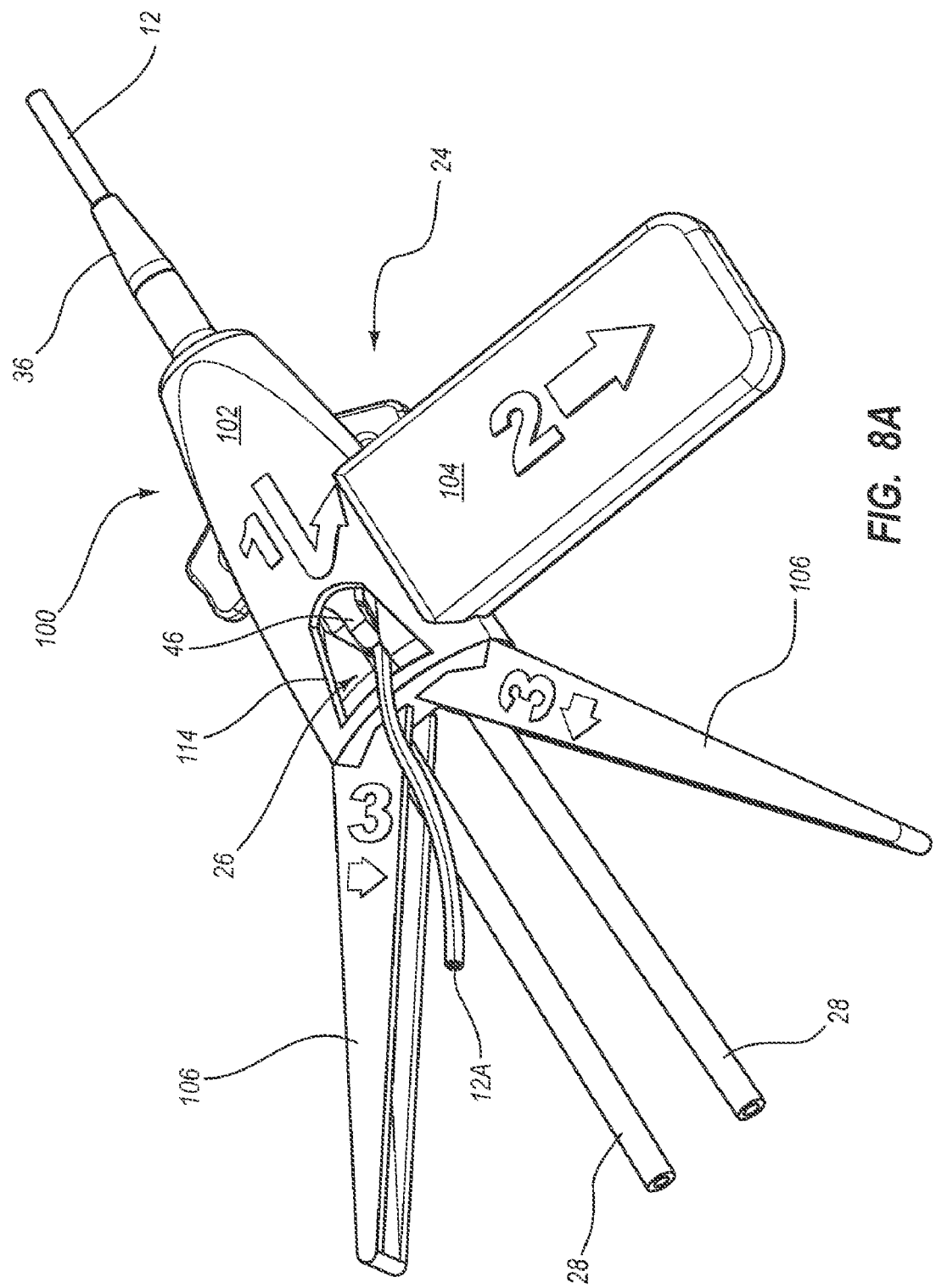
Figure 8B:
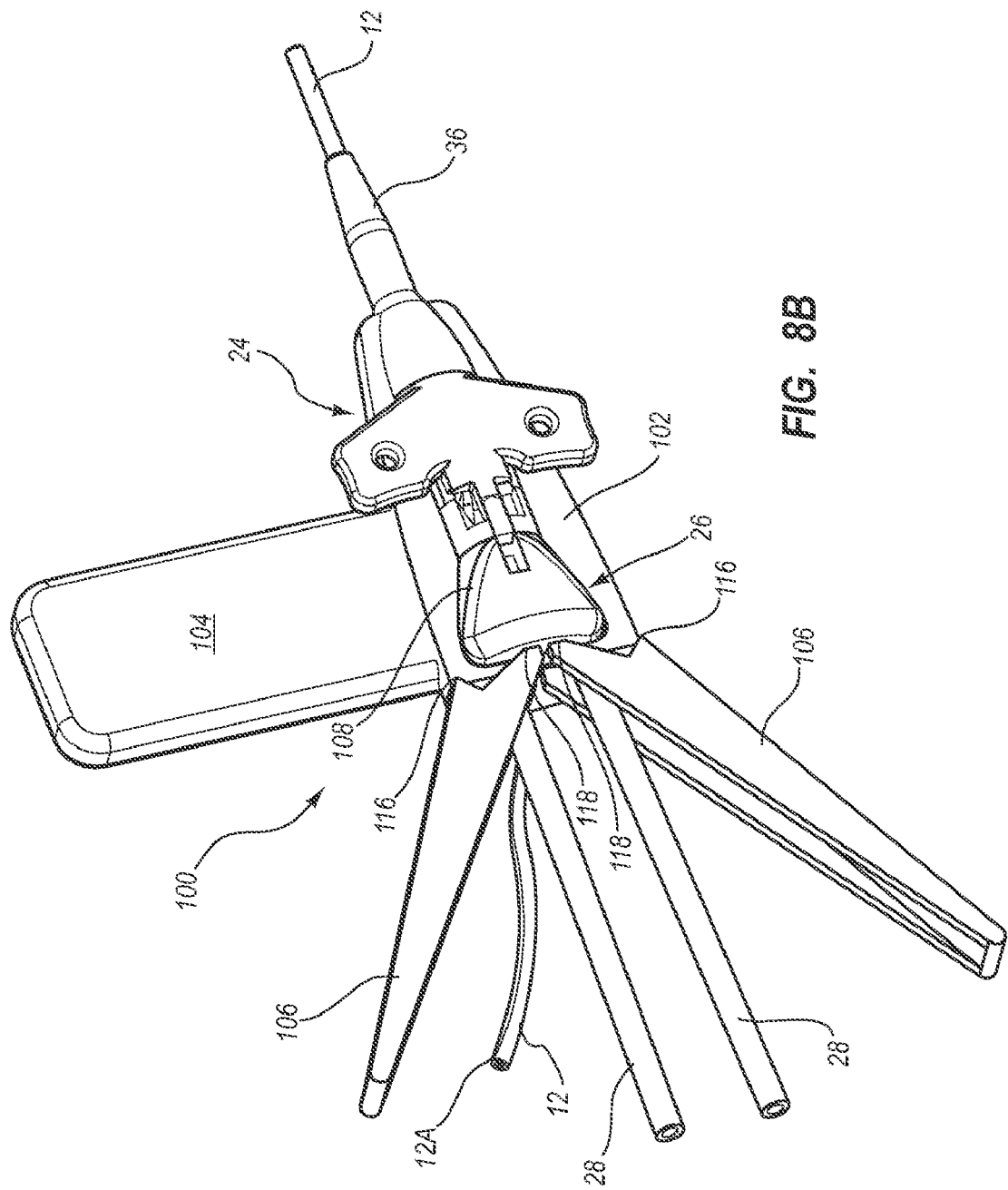
Figure 8D:
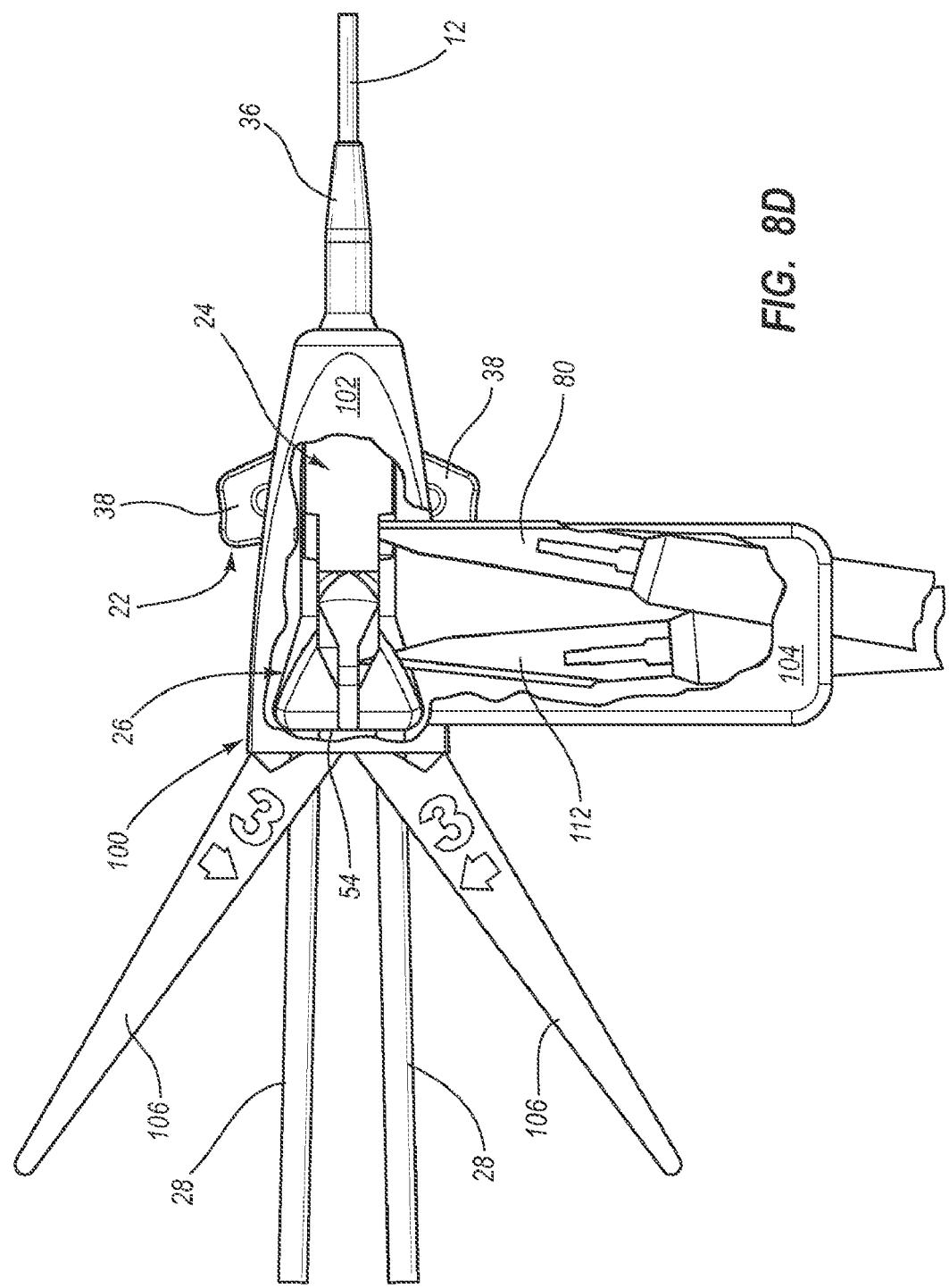

The cutting member housing 104 is removably attached to the assembly tool main body 102. As mentioned further above, the cutting member housing 104 houses the first cutting member 80, as shown in FIG. 8D such that the first cutting member extends through the notch 56 in the proximal hub portion body 50 (FIG. 6A) when the proximal hub portion 26 is disposed within the assembly tool cavity 108. As mentioned, this enables the first cutting member 80 to cross sectionally slice the catheter tube 12 as it passes through the hub 22 during distal hub advancement along the catheter tube.

The cutting member housing 104 further includes a second cutting member 112 that is positioned such that a tip 112A thereof extends through the proximal hub portion body 50 and into the cavity 52, as shown in FIG. 8E. So positioned, and with the its cutting surface facing proximally, the tip 112A of the second cutting member 112 is employed to trim off the portions of the catheter tube 12 extending from the proximal hub portion cavity 52 (FIG. 6B) after the tube has been sliced by the first cutting member 80 during distal advancement of the hub 22 along the catheter tube. Further details regarding catheter tube trimming by the second cutting member 112 are given further below. Note that the main body 102 of the assembly tool 100 includes a window 114 to enable the sliced portions of the catheter tube 12 extending from the hub portion cavities 32, 52 to extend through the assembly tool (see, e.g., FIG. 9A).

The lever arms 106 of the assembly tool 100 are lever components employed to lockingly mate the distal hub portion 24 and the proximal hub portion 26 to each other after the hub 22 has been slid along the catheter tube 12 to a desired location. As best seen in FIGS. 8C and 8D, in the present embodiment each lever arm 106 includes a hinge point 116, at which point the lever arm is hingedly connected to the main body 102 of the assembly tool 100, and an engagement surface 118.

As will be described in further detail below, as the lever arms 106 are pinched squeezed together the engagement surface 118 of each lever arm pushes against the base surface 54 of the proximal hub portion 26. This causes the distal hub portion 24 to fully engage the proximal hub portion 26, in turn causing the connector latches 62 of the proximal hub portion to engage with the corresponding receptacles 42 of the distal hub portion 24 and the connector latch 40 thereof to engage with the receptacle 60 of the proximal hub portion, thus locking the two hub portions together. Locking of the distal and proximal hub portions 24, 26 also causes a compressive fit to be established between the tube pins 70 and the uncut proximal portion of the catheter tube 12, as will be details further below. As mentioned, it is appreciated that other levered and non-levered structures can be employed for causing the mating of the two hub portions as described herein; as such, the present discussion should not be considered limiting.

Reference is now made to FIGS. 9A-9D in describing placement and locking of the hub 22 about the catheter tube 12 of the catheter 10 as part of a procedure for placing the catheter within the body of the patient 18 (FIG. 1), according to one embodiment. Note again that the hub, assembly tool, and method described herein can be adapted for use with other catheters and tubular medical devices for placement within a patient.

Figure 9A:
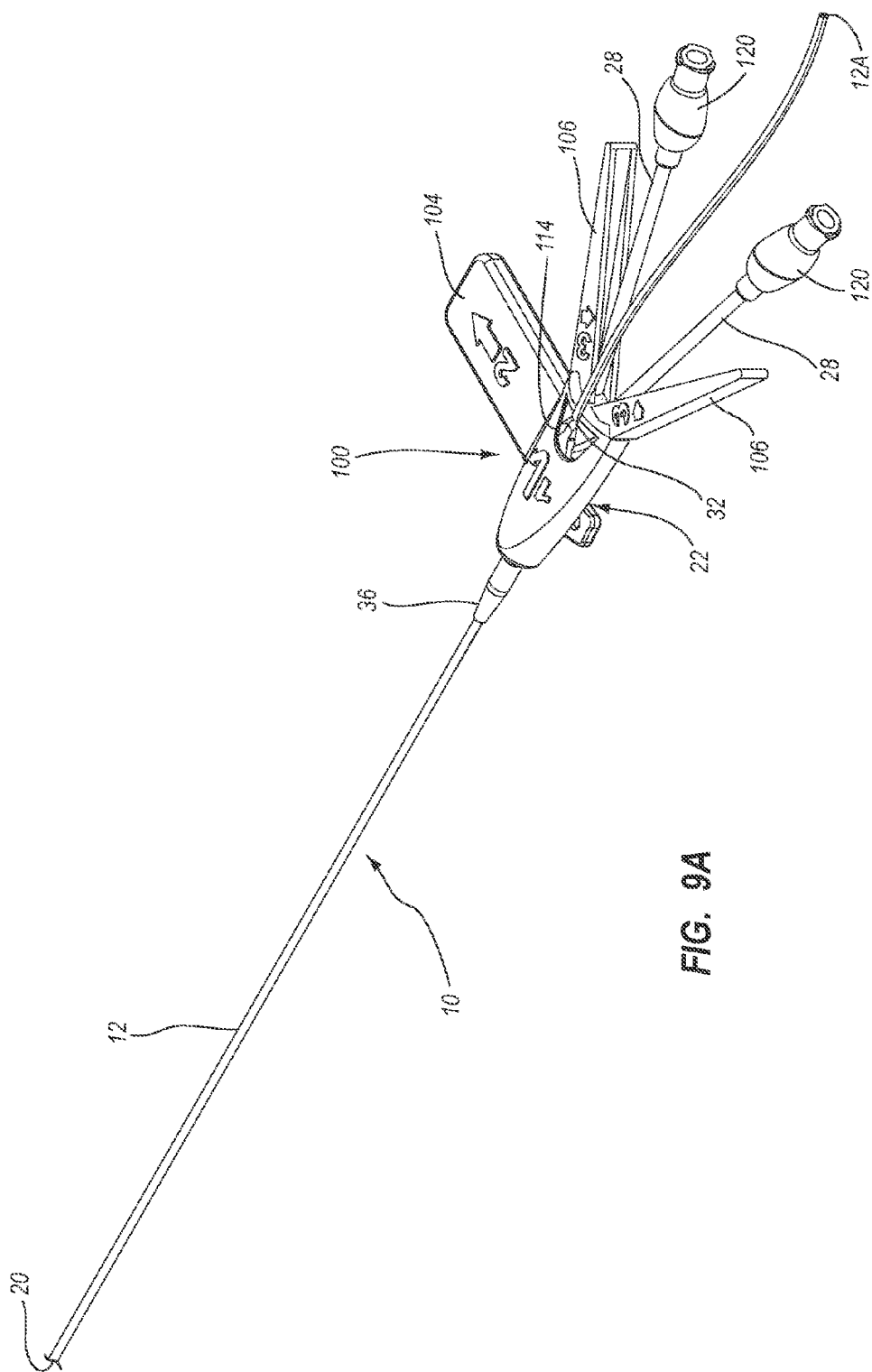
FIGS. 9A-9D are various views of use of the hub and assembly tool of FIGS. 8A-8E in placing and trimming a catheter.

The catheter 10 can be configured before placement with the catheter hub 22 generally positioned with respect to the catheter tube 12 as shown in FIG. 9A and with the assembly tool 100 disposed about the hub so as to maintain the distal and proximal hub portions 24, 26 in a desired state of proximate separation as shown in FIG. 2. A distal portion of the catheter tube 12 is inserted into the patient via the insertion site 20. The hub 22 and/or assembly tool 100 is then grasped and slid distally along the catheter tube 12 toward the insertion site 20, as indicated by the arrow in FIG. 9B (note that any stylet or guidewire included in one or both of the catheter tube lumens 14 is first removed before hub advancement). This causes portions of the catheter tube 12 to pass through the conduits 34 and 68 defined in the distal hub portion 24 and proximal hub portion 26, respectively (FIGS. 3A, 3C, 5), and past the first cutting member 80 (FIGS. 6A, 6B), which extends into the hub portion cavities 32, 52 from the cutting member housing 104 (FIG. 8D).

Figure 9B:
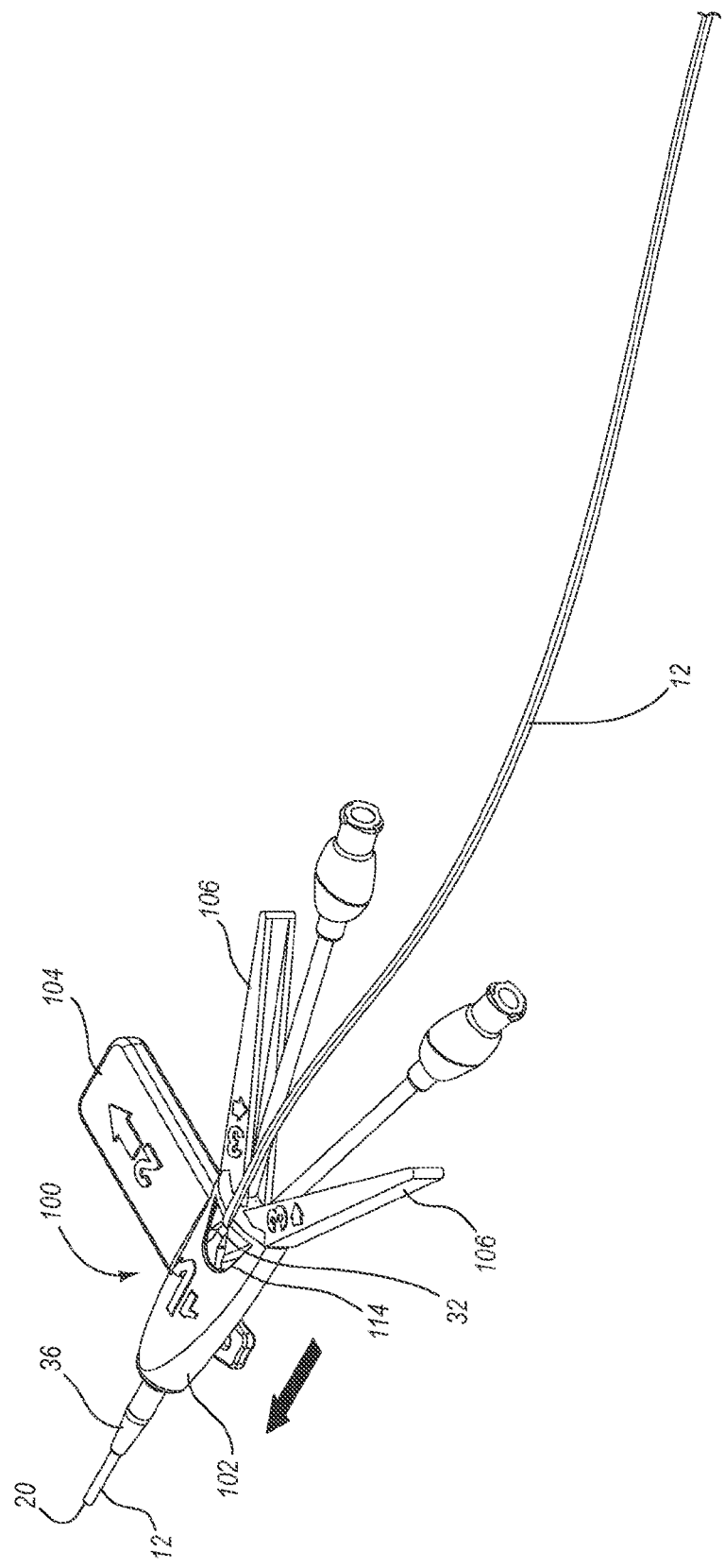

Passage of the catheter tube 12 past the first cutting member 80 causes cutting and splitting of the catheter tube into two pieces, thus enabling distal portions 70B of the tube pins 70 to remain within the uncut portion of the catheter tube lumens 14 (FIGS. 5-6B) while the hub 22/assembly tool 100 is distally advanced. The split pieces of the catheter tube 12 exit the hub portion cavities 32, 52 and out through the assembly tool window 114 (FIG. 9B). Note that the distal movement of the hub 22 along the catheter tube 12 toward the catheter insertion site 20 results in the split tube advancing out the assembly tool window 114.

Figure 9C:
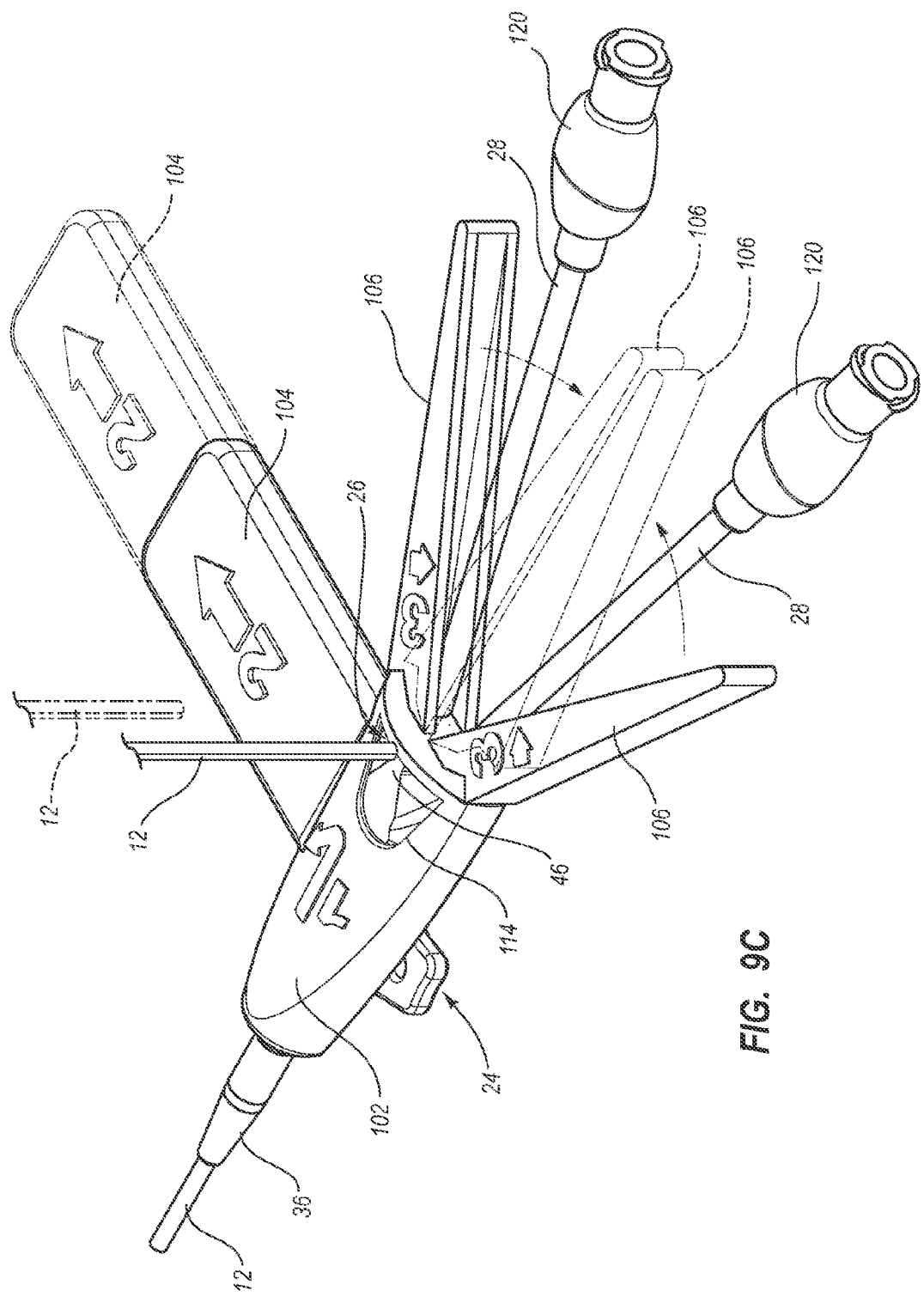

As shown in FIG. 9C, once the hub 22/assembly tool 100 has been advanced to a desired position with respect to the insertion site 20, the split catheter tube 12 extending from the proximal hub portion cavity 52 via the assembly tool window 114 is pulled as indicated by the arrow disposed on the assembly tool main body 102 such that a portion of the split catheter tube proximate the tip 112A of the second cutting member 112 (FIG. 8E) is cut by the cutting member tip, thus separating it from the catheter 10 and enabling it to be discarded.

With the first and second cutting members 80, 112 no longer needed, the cutting member housing 104 can then be removed from the assembly tool 100 (FIG. 9C), which removes both cutting members from the hub 22 and assembly tool. The cutting member housing can be disposed of. In one embodiment, a blade safety mechanism can be included to protect the user from the cutting members 80, 112 when the cutting member housing 104 is removed. Note that in one embodiment, the cutting member housing can include only one of the two cutting members. In another embodiment, one or both of the cutting members can be removably or permanently integrated into one of the hub portions itself, or the cutting members can be combined into a single component. In yet another embodiment, no assembly tool is included with the hub.

Finally, the lever arms 106 are actuated by pinching them together, as shown in FIG. 9C, in order to lockingly mate the distal and proximal hub portions 24, 26 together, as has been described. Mating of the hub portions 24, 26 in this manner further causes actuation of the compression washers 66. In particular, mating of the distal and proximal hub portions 24, 26 causes the invertible compression washers 66 to become compressed between the actuation surface 44 of the distal hub portion (FIG. 3C) and the compression support member 64 (FIG. 4E). This compression causes the actuation surface 44 to engage the most proximate compression washer and cause it and the other washers to invert, or fold in on themselves. This reduces the inner diameter of each compression washer 66, which in turn compresses the catheter tube 12 passing through the inner diameter against the distal portion 70B of the tube pins 70 disposed within the catheter tube lumens 14, thus fluidly sealing the tube pins within the catheter tube lumens and preventing fluid leakage from the interface. Note that a distal surface of the compression support member 64 includes a chamfered surface 64A that substantially matches the shape of the most proximal compression washer 66 after inversion thereof, as best seen in FIG. 5.

Thus it is seen that the compression washers serve as one example of a means for fluidly sealing a tube pin within a catheter lumen. It is appreciated, however, that other means can also be employed to accomplish the desired functionality as appreciated by one skilled in the art. For example, compression rings or collets of varying configurations can be employed in one embodiment. Note also that, though locking of the hub portions and compression of the tube pin/catheter lumen interface occurs in a single stage, in other embodiments these actions can occur separately in sequence. Note further that, in one embodiment, the distal and proximal hub portions can be locked together manually, i.e., without mechanical tool assistance, that the hub can include more than two portions, or that the hub can include a single piece that does not require locking together.

Figure 9D:
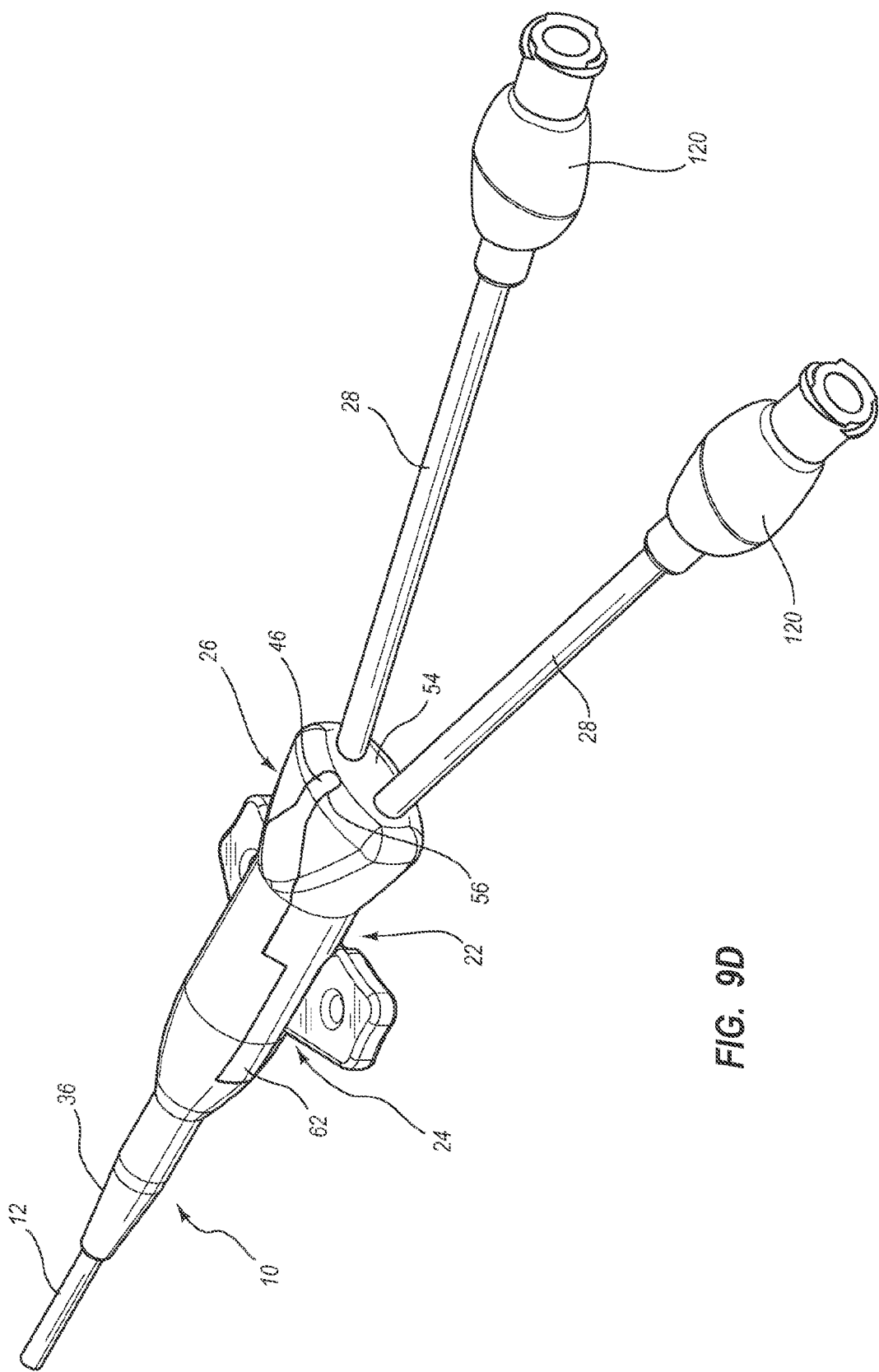

Once the hub 22 has been positioned and locked into place on the catheter tube 12, the assembly tool 100 can be removed from the hub, resulting in the catheter 10 configured as shown in FIG. 9D, including connectors 120 for connecting the catheter to suitable apparatus.

While certain representative embodiments and details have been shown for purposes of illustrating aspects contemplated by the instant disclosure, it will be apparent to those skilled in the art that various changes in the methods and apparatus disclosed herein may be made without departing from the scope contemplated by the instant disclosure, which is defined in the appended claims.

What is claimed is:

1. A tubular medical device for placement of a portion thereof into a body of a patient, the medical device, comprising:
   an elongate tube defining at least one lumen;
   at least one extension tube; and
   a hub for placing the at least one extension tube in fluid communication with the at least one lumen of the elongate tube, the hub being axially slidable along the elongate tube in a first unlocked state, the hub including:
      at least one tube pin in fluid communication with the at least one extension tube;
      means for cutting a proximal portion of the elongate tube such that a portion of the at least one tube pin remains within an uncut portion of the at least one lumen during sliding of the hub along the elongate tube, the means for cutting being at least temporarily included with the hub; and
      means for fluidly sealing the at least one tube pin within the at least one lumen when the hub is locked into a second locked state such that the hub is no longer slidable along the elongate tube and such that the at least one extension tube is in fluid communication with the at least one lumen of the elongate tube via the at least one tube pin.

2. The tubular medical device as defined in claim 1, wherein the means for fluidly sealing compressively seals an interface of the at least one tube pin within the at least one lumen.

3. The tubular medical device as defined in claim 2, wherein the means for fluidly sealing includes at least one annular compression washer disposed about the catheter tube proximate the interface of the at least one tube pin within the at least one lumen, the at least one compression washer being invertable between first and second positions, an inner diameter of the at least one compression washer being relatively smaller in the second position than in the first position.

4. The tubular medical device as defined in claim 1, wherein the means for cutting is included with an assembly tool disposed about the hub during placement thereof, the means for cutting being removable from the assembly tool.

5. The tubular medical device as defined in claim 1, wherein the means for cutting splits the elongate tube into at least two longitudinal pieces.

6. A catheter, comprising:
   an elongate catheter tube defining at least one lumen;
   at least one extension tube; and
   a hub for placing the at least one extension tube in fluid communication with the at least one lumen of the catheter tube, the hub being axially slidable along the catheter tube when in a first unlocked state, the hub including:
      at least one tube pin in fluid communication with the at least one extension tube; and
      a first cutting member at least temporarily included with the hub for longitudinally cutting the catheter tube during axial sliding of the hub along the catheter tube such that a distal portion of the at least one tube pin remains disposed within the at least one lumen of an uncut portion of the catheter tube,
      wherein the hub is lockable into a second locked state such that the hub is no longer axially slidable along the catheter tube and the at least one extension tube is in fluid communication with the at least one lumen of the catheter tube via the at least one tube pin.

7. The catheter as defined in claim 6, further comprising:
   a compression element to fluidly seal the at least one tube pin within the at least one lumen.

8. The catheter as defined in claim 7, wherein the compression element includes an invertable compression washer.

9. The catheter as defined in claim 7, wherein the hub includes a distal hub portion and a proximal hub portion, wherein the compression element is initially included with the proximal hub portion, and wherein the distal and proximal hub portions include latching features for engaging one another when the hub is placed into the second locked state.

10. The catheter as defined in claim 6, wherein the first cutting member includes a blade positioned proximal to at least a portion of the at least one tube pin, and wherein the first cutting member is removable from the hub after use.

11. The catheter as defined in claim 6, further comprising:
   a second cutting member for trimming a proximal portion of the catheter after the hub is positioned in a desired location on the catheter tube, wherein the first and second cutting members are included with an assembly tool, the assembly tool removably attached to the hub.

12. A method for proximally trimming a catheter, the catheter including an elongate catheter tube defining at least one lumen, the method comprising:

placing at least a distal portion of the catheter tube within a body of a patient;

sliding a hub in a distal direction along the catheter tube, the catheter tube received by a conduit of the hub, the hub including at least one tube pin including a portion that remains within the at least one lumen of the catheter tube during the sliding of the hub;

axially cutting a proximal portion of the catheter tube during the sliding of the hub; and sealing an interface between the at least one tube pin and the at least one lumen after the hub is disposed at a desired position such that fluid communication is established between the at least one lumen of the catheter tube and at least one extension tube of the catheter via the at least one tube pin.

13. The method for proximally trimming as defined in claim 12, wherein the hub includes a distal hub portion and a proximal hub portion, wherein the distal and proximal hub portions are unlocked with respect to one another during sliding of the hub, and wherein the method further comprises:

locking the distal and proximal hub portions together after the hub is disposed at the desired position.

14. The method for proximally trimming as defined in claim 13, wherein locking the distal and proximal hub portions together further includes actuating at least one lever component to lock the hub portions together and wherein locking the distal and proximal hub portions together further causes the sealing of the interface between the at least one tube pin and the at least one lumen of the catheter tube.

15. The method for proximally trimming as defined in claim 14, wherein sealing the interface further comprises:

compressing the interface between the at least one tube pin and the at least one lumen with a compression component included with the proximal hub portion.

16. A catheter, comprising:

an elongate catheter tube defining a plurality of lumens;

a hub including a distal hub portion and a proximal hub portion, the distal and proximal hub portions defining a conduit through which the catheter tube is received;

a plurality of extension tubes;

a plurality of tube pins included with the hub assembly, each tube pin being in fluid communication with a corresponding one of the extension tubes; and an assembly tool removably included with the hub and including:

a first cutting member positioned to cut a proximal portion of the catheter tube along a length thereof as the hub is moved distally along the catheter tube such that a portion of each of the tube pins remains disposed within an uncut portion of a respective one of the lumens of the catheter tube and such that each extension tube is in fluid communication with at least one of the lumens of the catheter tube; and at least one lever component for locking the distal and proximal hub portions together to prevent further movement of the hub along the catheter tube after the hub is positioned in a desired location.

17. The catheter as defined in claim 16, further comprising an annular compression element for fluidly sealing an interface between the plurality of tube pins and the lumens of the catheter tube, the compression element component including at least one invertable compression washer disposed about the catheter tube, wherein inversion of the at least one compression washer is at least partially actuated by actuation of the at least one lever component.

18. The catheter as defined in claim 17, wherein the at least one lever component includes two lever arms hingedly connected to the assembly tool, each lever arm including an engagement surface for engaging a portion of the proximal hub portion during locking with the distal hub portion.

19. The catheter as defined in claim 18, wherein the assembly tool includes a second cutting member for removing portions from the catheter tube already cut by the first cutting member, the first and second cutting members included in a cutting member housing that is removable from the assembly tool.

20. A method for proximally trimming a catheter after insertion thereof into a patient, the catheter including a catheter tube defining at least one lumen, the method comprising:

providing an assembly tool removably included with a hub, the assembly tool including a first cutting member and a second cutting member;

longitudinally cutting a proximal portion of the catheter tube during advancement of the hub distally along the catheter tube such that a portion of a tube pin of the hub for providing fluid access to the at least one lumen remains within the at least one lumen during advancement of the hub;

removing the assembly tool from the hub; and sealing an interface between the tube pin and the at least one lumen of the catheter tube.

* * * * *